United States Patent
Bonnette et al.

(10) Patent No.: US 8,951,229 B2
(45) Date of Patent: Feb. 10, 2015

(54) PRESSURE ACTUATED CATHETER SEAL AND METHOD FOR THE SAME

(75) Inventors: Michael J. Bonnette, Minneapolis, MN (US); Eric J. Thor, Arden Hills, MN (US); Stephen E. Weisel, Brook Park, MN (US); Arthur E. Uber, III, Pittsburgh, PA (US); Leif E. Leirfallom, Plymouth, MN (US); Laszlo T. Farago, Hudson, WI (US)

(73) Assignee: Boston Scientific Limited, Hamilton (BM)

( * ) Notice: Subject to any disclaimer, the term of this patent is extended or adjusted under 35 U.S.C. 154(b) by 879 days.

(21) Appl. No.: 13/032,185

(22) Filed: Feb. 22, 2011

(65) Prior Publication Data

US 2011/0208129 A1    Aug. 25, 2011

Related U.S. Application Data

(60) Provisional application No. 61/306,645, filed on Feb. 22, 2010.

(51) Int. Cl.
*A61M 5/178* (2006.01)
*A61M 5/00* (2006.01)
(Continued)

(52) U.S. Cl.
CPC ..... *A61M 39/0613* (2013.01); *A61M 2039/062* (2013.01)
USPC ............ 604/167.02; 604/164.01; 604/167.01; 604/246; 604/247; 604/256; 604/533; 604/534; 604/535; 604/537

(58) Field of Classification Search
CPC .......... A61M 25/007; A61M 25/0606; A61M 2039/0054; A61M 2039/0072; A61M 39/06; A61M 39/0613; A61M 2039/062; A61M 2039/0686

USPC ............. 604/164.01, 164.02, 167.01, 167.02, 604/167.03, 167.04, 167.06, 246, 247, 256, 604/533, 534, 535, 537, 523, 539, 905
See application file for complete search history.

(56) References Cited

U.S. PATENT DOCUMENTS 4,946,133 A  *  8/1990  Johnson et al. ............ 251/149.1
5,125,915 A     6/1992  Berry et al.
(Continued)

FOREIGN PATENT DOCUMENTS

EP        0308815 B1    7/1994

OTHER PUBLICATIONS

Supplementary European Search Report from related application dated Jun. 1, 2007.
(Continued)

*Primary Examiner* — Kevin C Sirmons
*Assistant Examiner* — Shefali Patel
(74) *Attorney, Agent, or Firm* — Seager, Tufte & Wickhem, LLC

(57) ABSTRACT

A catheter includes a pressure actuated seal within a manifold. A catheter body is coupled with the manifold, and a manifold lumen and a catheter lumen are configured to receive pressurized fluids. The pressure actuated seal includes a pressure actuated seal element having a seal element lumen. The seal element lumen is in communication with the manifold and catheter lumens. The pressure actuated seal element is deformable between an open configuration and a sealed configuration. In the sealed configuration, the pressurized fluids in the manifold press on the pressure actuated seal element along a first seal face. The pressure actuated seal element compresses inwardly around the seal element lumen according to a pressure of the pressurized fluids. In the open configuration, the pressure actuated seal element relaxes in an absence of the pressurized fluids, and the seal element lumen is open and configured to allow passage of an instrument.

30 Claims, 17 Drawing Sheets

(51) Int. Cl.
*A61M 5/14* (2006.01)
*A61M 25/16* (2006.01)
*A61M 25/18* (2006.01)
*A61M 39/00* (2006.01)
*A61M 39/10* (2006.01)
*A61M 39/06* (2006.01)

(56) References Cited

U.S. PATENT DOCUMENTS

| | | |
|---|---|---|
| 5,167,637 A | 12/1992 | Okada et al. |
| 5,205,831 A | 4/1993 | Ryan et al. |
| 5,205,834 A | 4/1993 | Moorehead et al. |
| 5,259,842 A | 11/1993 | Plechinger et al. |
| 5,478,331 A | 12/1995 | Heflin et al. |
| 5,507,732 A | 4/1996 | McClure et al. |
| 5,556,387 A * | 9/1996 | Mollenauer et al. .......... 604/249 |
| 5,810,869 A | 9/1998 | Kaplan et al. |
| 5,895,376 A | 4/1999 | Schwartz et al. |
| 5,957,901 A * | 9/1999 | Mottola et al. ................. 604/264 |
| 6,024,729 A | 2/2000 | Dehdashtian et al. |
| 6,197,016 B1 | 3/2001 | Fourkas et al. |
| 6,287,280 B1 | 9/2001 | Lampropoulos et al. |
| 6,299,132 B1 | 10/2001 | Weinheimer et al. |
| 6,344,031 B1 | 2/2002 | Novacek et al. |
| 6,609,696 B2 | 8/2003 | Enerson |
| 7,226,433 B2 | 6/2007 | Bonnette et al. |
| 2003/0066978 A1 | 4/2003 | Enerson |
| 2003/0094429 A1 | 5/2003 | Sudo et al. |
| 2004/0172008 A1 | 9/2004 | Layer |
| 2006/0229564 A1 | 10/2006 | Andersen et al. |
| 2007/0073242 A1 | 3/2007 | Andersen et al. |
| 2008/0255651 A1 | 10/2008 | Dwork |
| 2008/0289181 A1 * | 11/2008 | Kozak et al. ............... 29/890.09 |

OTHER PUBLICATIONS

Communication from European Patent Office from related application dated Sep. 5, 2007.

* cited by examiner

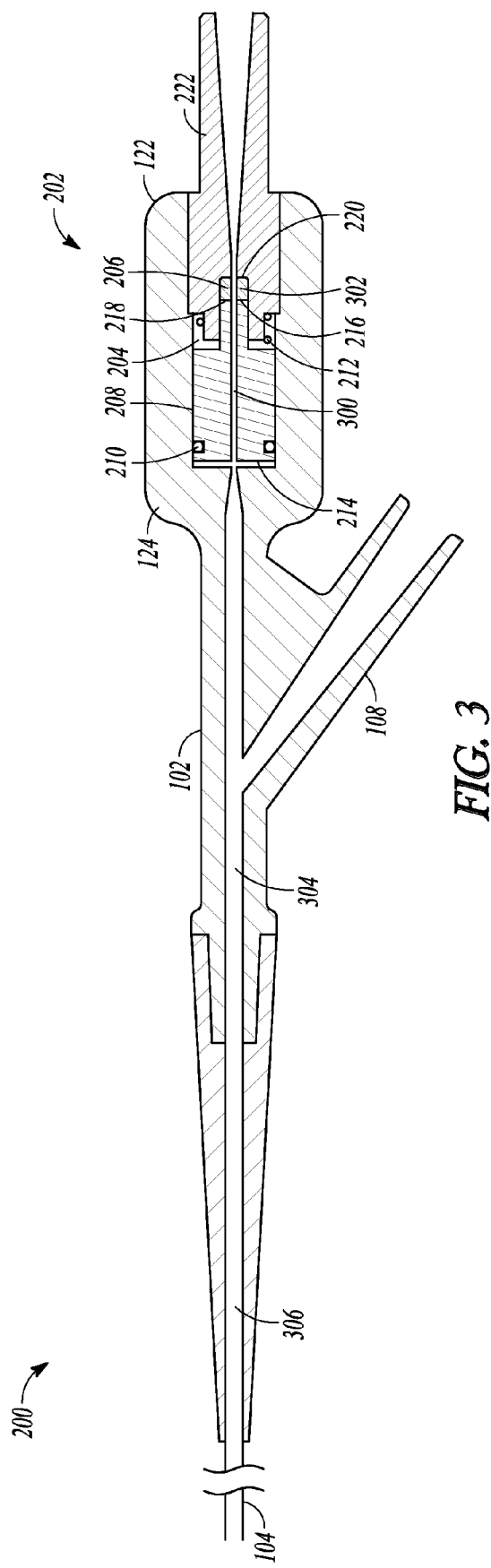
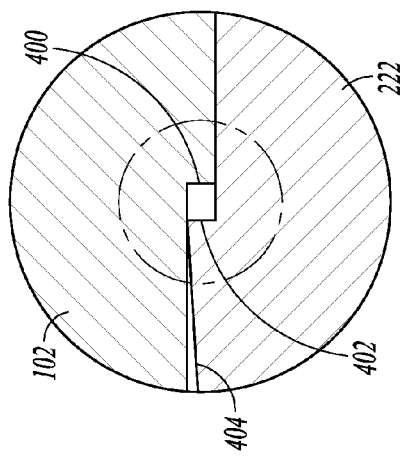
FIG. 3
FIG. 4

PRESSURE ACTUATED CATHETER SEAL AND METHOD FOR THE SAME

CROSS-REFERENCE TO RELATED APPLICATIONS

This application is a non-provisional of U.S. Application No. 61/306,645 filed Feb. 22, 2010, the contents of which are incorporated herein by reference.

TECHNICAL FIELD

Catheter and catheter lumen seals.

BACKGROUND

Catheter assemblies include lumens for the delivery of instruments and fluids to treatment areas within the body. It is sometimes necessary to seal the lumen to prevent the escape of fluids or provide a sealed environment isolated from exterior contaminants. In some examples, catheters include manually operated seal assemblies within catheter handles and manifolds. The manually operated seal assemblies are operated with mechanisms that turn nuts, close clamps, push pistons and the like to deform a seal element and close a lumen. Each of these mechanisms require a free hand or other device to seal the assembly. Further, the mechanisms require additional manual operation to disengage the seal and allow access to the lumen. Manually operated seals are particularly difficult to use during a procedure where the user's hands are dedicated to manipulating the catheter and other instruments. For instance, where the user needs to direct full attention to manipulation of a catheter including a manually operated seal the user must disengage or adjust the position of at least one hand to manipulate the seal and thereby may lose the previous orientation of a catheter already navigated or partly navigated through vasculature. Continued navigation or repositioning of the catheter may be required with possible frustration to the purpose of the procedure.

Additionally, the manual mechanisms fail to seal the lumen according to the pressure developed within the catheter assembly. Stated another way, the manually operated seal assemblies create a seal according to the mechanism used, for instance, according to the hand tightening of a nut without any assurance the seal will withstand a pressurized environment, such as fluids under pressure. These manual mechanisms may thereby be subject to complications including fluid leaks from the pressurized environment of the catheter or ingress of contaminants. Further, there is no clear indication to a user—other than an ambiguous resistance to further tightening—that a seal is formed. Without a clear indication of the status of a seal, undesirable leaking of fluids (including body fluids such as blood) and ingress of contaminants may occur without the knowledge of the user.

SUMMARY

The pressure actuated seal assemblies and methods for using the same described herein automatically seal a seal element lumen in the presence of a pressurized fluid without requiring hand operation from a catheter operator. The operator does not need to operate the seal or observe an indicator to know the pressure actuated seal assembly is sealed and closing the seal element lumen. Instead, when a pressurized fluid is introduced to the catheter and manifold for use as part of a procedure the seal assembly automatically closes because of the pressure. The operator can thereby confidently operate the catheter without doubting whether the seal has closed the seal element lumen or the seal was not actuated because of operator error. Additionally, because the seal element is actuated according to the fluid pressure within the catheter the seal becomes correspondingly tighter with increasing fluid pressures. A seal is thereby maintained within the seal element lumen across a range of pressures. For instance, the pressure actuated seal assemblies described herein provide a complete seal from at least 10 to 1200 psi. Optionally a complete seal is maintained over pressures greater than 1200 psi. Similarly, the pressure actuated seal elements automatically unseal in the absence of a pressurized fluid freeing the operator from manipulating seal element into an open configuration.

Further, the seal element described herein is capable of closing the seal element lumen with or without an instrument therein. The seal element seals around a variety of instrument sizes and configurations (guidewires with varying diameters, multiple instruments and the like). For instance, a single seal element will seal around a variety of instruments with different perimeters when under pressure from fluid in the catheter body. In another example, the seal element material and seal element lumen size are chosen according to the size of the instrument delivered through the seal element. Stated another way, the seal element is chosen to ensure tight sealing around a specified instrument when the seal element is subjected to pressure from the pressurized fluid in the catheter body.

If a procedure requires the presence of an instrument within the catheter while the pressurized environment is maintained the instrument is fed into the catheter through the seal element. As the pressurized fluid applies pressure to the seal element the seal element closes and seals around the instrument. Optionally, sealing of the seal element fixes the instrument in place and correspondingly retains the instrument in a desired orientation according to the needs of the operator. In another example, the instrument is slidable through the closed seal element if movement of the instrument is necessary while the fluid is pressurized in the catheter. In any case, when the fluid in the catheter body is no longer pressurized and the seal element is open and the instrument is easily slidable through the seal element lumen.

BRIEF DESCRIPTION OF THE DRAWINGS

FIG. 3 is a cross-sectional view of the manifold of the catheter shown in FIG. 2.

FIG. 4 is a detailed cross-sectional view of element A in FIG. 3.

DESCRIPTION OF THE EMBODIMENTS

In the following detailed description, reference is made to the accompanying drawings which form a part hereof, and in which is shown by way of illustration specific embodiments of the present disclosure may be practiced. These embodiments are described in sufficient detail to enable those skilled in the art to practice aspects of this disclosure, and it is to be understood that other embodiments may be utilized and that structural changes may be made without departing from the scope of the present disclosure. Therefore, the following detailed description is not to be taken in a limiting sense, and the scope of the present disclosure is defined by the appended claims and their equivalents.

Figure 1:
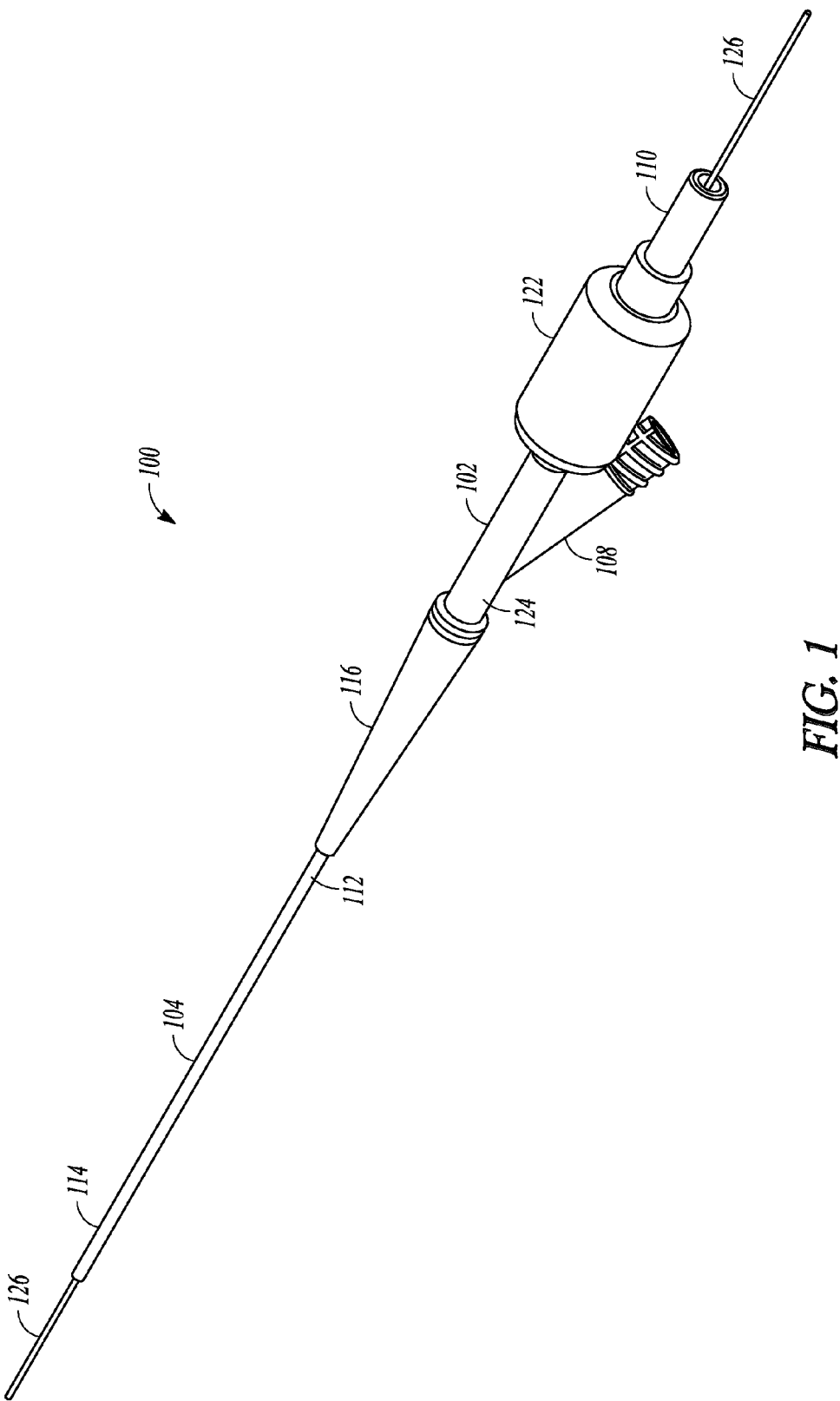
FIG. 1 is a partially exploded view of one example of a catheter assembly.

FIG. 1 shows one example of a catheter 100, such as a thrombectomy catheter. The catheter 100 includes a manifold 102, the manifold 102 is sized and shaped for connection with a high pressure fluid source. Optionally, the manifold 102 is configured for coupling with an exhaust reservoir for collection of fluids and thrombus removed from the body of a patient. A catheter body 104 is connected with the manifold 102. As shown in FIG. 1, the catheter body 104 extends between a catheter proximal portion 112 coupled with the manifold 102 and a catheter distal portion 114. In one example, a strain relief fitting 116 is coupled between the catheter body 104 and the manifold 102 to provide support and facilitate the connection of the catheter body with the manifold. Referring again to the manifold 102, as shown in FIG. 1, the manifold includes a high pressure passage 108 extending into the manifold 102. An introducer 110 is shown at a manifold proximal portion 122. The introducer 110 facilitates the introduction of instruments including guide wires, catheters and the like into the manifold 102 and from the manifold into the catheter body 104. One example of a guidewire 126 is shown in FIG. 1. As described in further detail below, the catheter 100 includes a series of lumens extending through the manifold 102 and the catheter body 104. For instance, the manifold 102 includes a manifold lumen extending from the manifold proximal portion 122 to a manifold distal portion 124. The manifold lumen is in communication with a catheter lumen extending through the catheter body 104 from the catheter proximal portion 112 to the catheter distal portion 114. These passages, including at least one of the manifold lumen and the catheter lumen, are sealed with pressure actuated seal assemblies as described in further detail below. In one example, the pressure actuated seal assemblies seal around instruments, such as the guide wire 126, and substantially prevent the flow of fluids out of the manifold 102 and the introducer 110. Additionally, the overall catheter is described below in operation (shown in FIGS. 18A-C) to inject fluids through the catheter near the catheter distal portion 114. A variety of pressure actuated seals are described herein to facilitate this fluid injection function.

Figure 2:
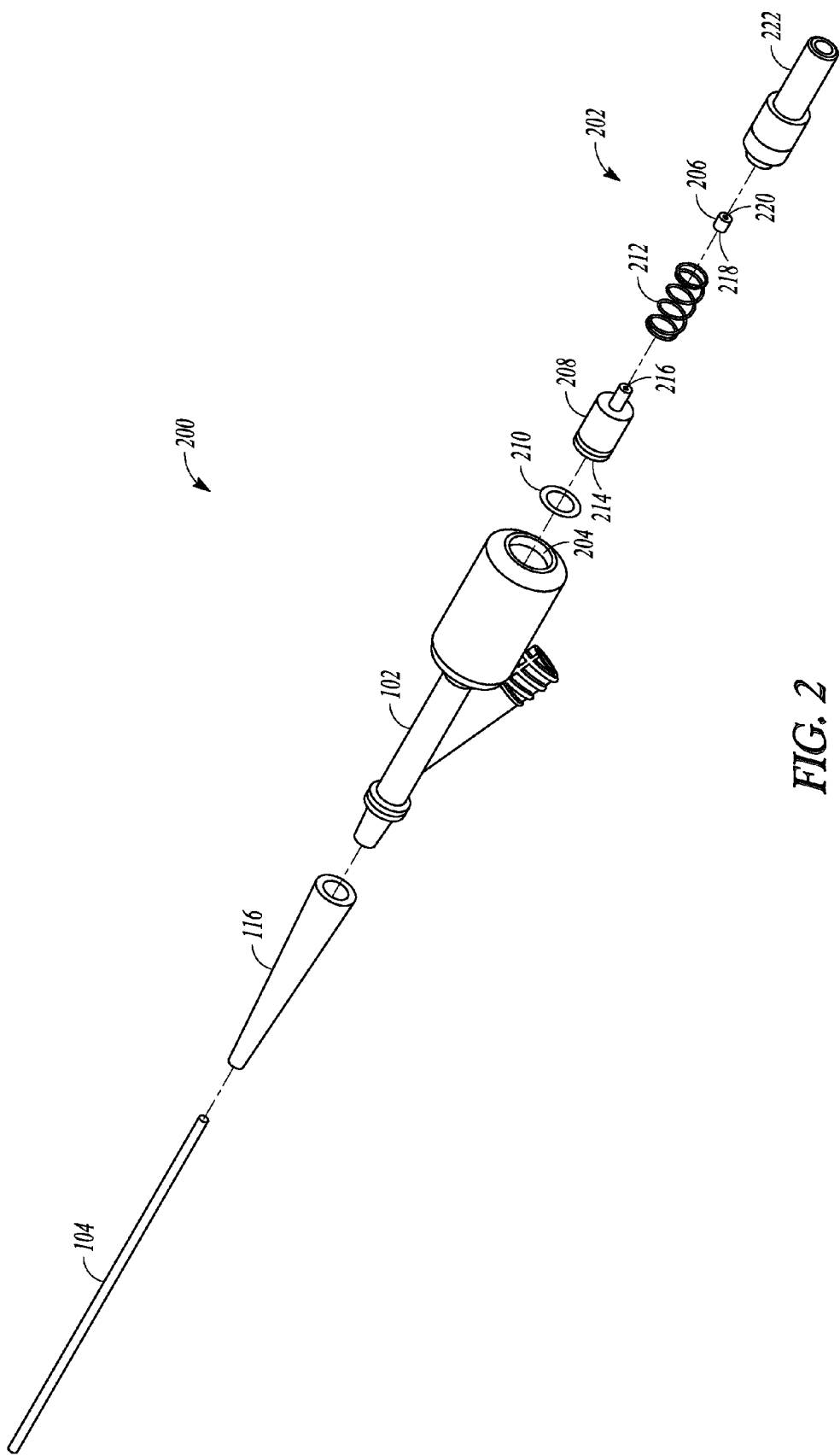
FIG. 2 is an exploded view of one example of a catheter including a pressure actuated seal assembly having an amplifier.

One example of a pressure actuated seal assembly is shown in FIG. 2. A catheter 200 is shown in FIG. 2 including the pressure actuated seal assembly 202. The pressure actuated seal assembly 202 includes a seal element 206 and an amplifier 208. As shown in further detail in FIG. 3 the amplifier 208 is positioned within a seal cavity 204 to assist in deforming the seal element 206 to close the seal element lumen 302 (shown in FIG. 3) through inward compression of the seal element 206 around the seal element lumen. In one example, the amplifier 208 includes an O-ring 210 coupled with the amplifier. The O-ring 210 slides along an interior surface of the seal cavity 204 and substantially prevents the passage of fluids around the amplifier 208. Pressurized fluids incident on the amplifier 208 thereby press the amplifier 208 into engagement with the seal element 206 without loss of pressure on the seal element 206 by flow of the fluid around the amplifier.

Referring again to FIG. 2, in one example, the pressure actuated seal assembly 202 includes a biasing element 212 such as a spring. The biasing element 212 is interposed between at least the amplifier 208 and the manifold 102. The biasing element 212 is sized and shaped to bias the amplifier 208 away from the seal element 206 in a relaxed state where pressurized fluids are not incident against the amplifier. The amplifier is thereby biased away from the seal element 206 allowing the seal element 206 to relax into its undeformed (e.g., open) orientation and allow smooth passage of instruments through the seal element and the amplifier 208. Depending upon the internal diameter of the seal element 206 and the outer diameter of the instrument (e.g., the guidewire 126), there is a seal formed and some friction between the instrument and the seal element 206 when the element 206 is in the undeformed orientation. As previously described in FIG. 1, the catheter 100 includes an introducer 110. The biasing element 212 is optional to the seal elements described herein. For instance, a biasing element is excluded where the seal element is inherently lubricious and readily resumes the undeformed configuration without sticking to manifold surfaces.

Referring now to FIG. 2, the catheter 200 includes an introducer guide 222 sized and shaped for coupling within a portion of the seal cavity 204. As shown in greater detail in FIG. 3, the introducer guide 222 engages with the manifold 102 (e.g., through snap fitting, threading and the like) and ensures the amplifier 208 and the seal element 206 are retained within the seal cavity 204 to hold the pressure actuated seal assembly 202 within the manifold 102.

The amplifier 208 includes a first amplifier face 214 and a second amplifier face 216. As shown in FIG. 2, the first and second amplifier faces 214, 216 are opposed to each other with the first amplifier face 214 directed toward the catheter body 104 and the second amplifier face 216 directed toward the seal element 206. The second amplifier face 216 is sized and shaped for engagement with the first seal face 218 of the seal element 206. A second seal face 220 is on an opposing side of the seal element 206 and directed toward the introducer guide 222. During operation pressurized fluids within the catheter body 104 and the manifold 102 exert pressure on the amplifier 208 and press the amplifier 208 into engagement with the seal element 206. Engagement of the amplifier 208 with the seal element 206 deforms the seal element and compresses it within the seal cavity 204. Compression of the seal element 206 within a correspondingly shaped recess within the seal cavity (e.g., the introducter guide 222) forces the seal element 206 to inwardly compress around the seal element lumen 302 shown in FIG. 3 because the seal element 206 has nowhere to expand. The pressurized fluids within the catheter body 104 that operate the seal element 206 include, but are not limited to, contrast media, saline, drugs, blood and other body fluids and the like.

Referring now to FIG. 3, the pressure actuated seal assembly 202 is shown in cross-section with the seal element 206 and amplifier 208 assembled in the seal cavity 204. The amplifier 208 is movable within the seal cavity 204 in proximal and distal directions according to the presence or absence of a pressurized fluid within the catheter body 104 and manifold 102. As shown in FIG. 3, a series of lumens extend through the catheter 200 including an amplifier lumen 300, the seal element lumen 302, the manifold lumen 304 and a catheter lumen 306. The lumens 300-306 are aligned and capable of fluid communication. Instruments including guide wires and the like are fed into the catheter 200 through the introducer guide 222 and received within the seal cavity 204 before being fed through the catheter body 104. For instance, in operation a guide wire is back loaded through the introducer guide 222 through the seal element lumen 302 (in the seal cavity), amplifier lumen 300, manifold lumen 304, catheter lumen 306 and through the catheter distal portion 114 shown in FIG. 1. In still another example, an instrument such as guide wire is front loaded through the catheter 200, for instance, through the catheter distal portion 114 into the catheter body 104, manifold 102 and through the amplifier lumen 300 and seal element lumen 302 and then out of the introducer guide 222.

In operation, at least the manifold 102 receives a pressurized fluid within the manifold lumen 304 through the high pressure passage 108. The pressurized fluid is distributed into the manifold 102 toward the amplifier 208. The pressurized fluid engages with the amplifier 208 and forces the amplifier proximally toward the seal element 206. The biasing force provided by the biasing member 212 is overcome by the force of the pressurized fluid allowing the proximal movement of the amplifier 208. In one example, because the of the O-ring 210 pressurized fluid is substantially prevented from moving around the amplifier 208 and into the remainder of the seal cavity 204. As the amplifier 208 is moved proximally toward the seal element 206 by the pressurized fluid the seal element 206 is deformed by the amplifier 208. Because the seal element 206 is held within a seal element cavity 310 (e.g., formed in the introducer guide 222 in one example) having a shape corresponding to the seal element deformation of the seal element 206 forces the seal element to constrict the seal element lumen 302 and tightly seal the seal element 206. Optionally, the fluid is pressurized gradually to slowly close the seal element 206. As the seal element 206 gradually closes some of the fluid including entrained air bubbles leaks through the seal element 206 out of the catheter lumen 306 and manifold lumen 304. Gradually applying pressure to the seal element 206 minimizes air bubbles within the system and correspondingly reduces the risk of emboli. Alternatively, the inner diameter of the seal element (e.g., the surface defining the seal element lumen 302) is sized to provide a residual seal around an instrument disposed therein when the fluid is not pressurized within catheter lumen 306. Optionally, the inner diameter of the seal element is sized to residually seal the seal element lumen 302 without pressurized fluid, and more tightly seal the lumen when pressurized fluid is present.

In another example, where one or more instruments are present within the seal element lumen 302 the seal element 206 constricts around the one or more instruments thereby closing the seal element lumen and preventing passage of the pressurized fluid beyond the seal element. In yet another example, where an instrument is not present within the seal element lumen 302, the seal element 206 is deformed by the amplifier 208 and compresses around the seal element lumen 302 to constrict and close the seal element lumen and substantially prevent passage of the pressurized fluids beyond the seal element. The seal element 206 is constructed with a pliable material including, but not limited to rubber, silicone, polyurethane, PEBAX (a registered trademark of the Ato Chimie Corp., France), synthetic latex, polyvinyl chloride, TEFLON (a registered trademark of E.I. Du Pont de Nemours and Company, Corp. Delaware) and the like. The pliable material of the seal element is selected with a particular durometer to seal around one or more of an instrument, multiple instruments or close the seal element lumen without an instrument present. In another example, the amplifier 208 is constructed of a more rigid material than the seal 206 for instance, including, but not limited to, hard resins, such as polycarbonate, metals and the like.

The first amplifier face 214 has a first surface area and the second amplifier face 216 has a second surface area less than the first surface area of the first amplifier phase 214 (See FIGS. 2 and 3). Force transmitted to the seal element by the amplifier 208 where the amplifier is pressed into the seal element by pressurized fluid is an amplified force based on the ratio of the first and second surface areas of the first and second amplifier faces 214, 216. The amplifier 208 thereby provides enhanced deformation and corresponding enhanced constriction of the seal element 206 around the seal element lumen 302 to provide a tight seal that reliably prevents the passage of the pressurized fluid through the seal element 302 whether an instrument is present or not. The seal element 206 is capable of sealing the seal element lumen 302 against fluid pressures of around 10 to 1200 psi.

Once the pressurized fluid within the catheter 200 is removed or depressurized the amplifier 208 relaxes within the seal cavity 204 and moves distally toward the catheter body 104 allowing the seal element 206 to assume a relaxed orientation and open the constricted seal element lumen 302 for passage of instruments and the like through the seal element lumen. To assist the distal movement of the amplifier 208 away from the seal element 206 the biasing element 212 coupled between the amplifier 208 and manifold 102 pushes the amplifier 208 away from the seal element 206. Without the pressurized fluid engaged against the amplifier 208, the biasing element 212 overcomes any residual seating of the amplifier against the seal element 206 through friction, interference fitting and the like. Stated another way, the biasing element 212 urges the amplifier 208 away from the seal element 206 thereby allowing the seal element to relax. The relaxed seal element 206 opens the seal element lumen 302 permitting the free passage of instruments including guide wires and the like through the lumens of the catheter 200.

The pressure actuated seal assembly 202 including the seal element 206 automatically seals the seal element lumen 302 in the presence of a pressurized fluid without requiring hand operation from a catheter operator or separate actuation of different mechanism to effect a seal. Stated, another way, the operator does not operate the seal or observe an indicator separately from the operation of the catheter (e.g., for a thrombectomy procedure). Instead, the seal element lumen 302 is closed by the seal element 206 as the working environment within the catheter body and the manifold is pressurized for the medical procedure. By consolidating the sealing function with the operation of the catheter 100 during the procedure, the operator does not need to confirm a seal is present or remove a hand from the catheter 100 for operation of a seal mechanism to confidently know the pressure actuated seal assembly 202 is sealed and closing the seal element lumen 302. Operator error including failure to operate a separately operable seal and undesirable non-therapeutic movement of the catheter as the operator adjusts a hand grip on the catheter or fully removes a hand to operate a seal are substantially avoided.

Moreover, because the seal element 206 is actuated according to the fluid pressure within the catheter 100 the seal becomes correspondingly tighter with increasing fluid pressures. A seal is thereby maintained within the seal element lumen 302 across a range of pressures. For instance, the pressure actuated seal assemblies described herein provide a complete seal from at least 10 to 1200 psi. Optionally a complete seal is maintained with pressures greater than 1200 psi. Similarly, the pressure actuated seal elements automatically unseal in the absence of a pressurized fluid freeing the operator from manipulating a seal element into an open configuration.

As described above, the pressure actuated seal assembly 202 including the seal element 206 is configured to automatically seal the seal element lumen 302 when the working environment within the catheter and manifold is pressurized. Similarly, each of the seal elements and the corresponding pressure actuated seal assemblies described herein automatically seal according to pressure increases within the manifold lumen and catheter lumens.

Additionally, the seal element 206 is described above as configured to seal around an instrument or instruments positioned within the seal element lumen 302. Further, the seal element 206 is described as configured to constrict around an empty seal element lumen 302 and thereby seal the seal element 206. Each of the seal elements and corresponding pressure actuated seal assemblies described herein are similarly capable of at least one or both of sealing around one or more instruments and sealing an empty seal element lumen.

Referring again to FIG. 3, the pressure actuated seal assembly 202 is assembled within a seal cavity 204 and held therein by the introducer guide 222. Referring now to FIG. 4, one example of the engagement features retaining the introducer guide 222 within the seal cavity of the manifold 102 is shown. The manifold 102 includes a manifold locking ridge 400 and the introducer guide 222 includes an introducer locking ridge 402. The manifold locking ridge 400 and introducer locking ridge 402 engage with each other to substantially prevent the proximal movement of the introducer guide 222 and decoupling of the guide from the manifold 102. A tapered barrel 404 is provided with the introducer guide 222 to facilitate sliding of the introducer guide 222 into the seal cavity 204 to assist in the temporary deformation of the manifold 102 to allow the distal passage of the introducer locking ridge 402 into the seal cavity 204 for engagement with the manifold locking ridge 400. Once assembled with the manifold locking ridge 400 engaged with the introducer locking ridge 402 the amplifier 208 and seal element 206 are positioned and held in the seal cavity 204 in the orientation shown in FIG. 3.

Figure 5:
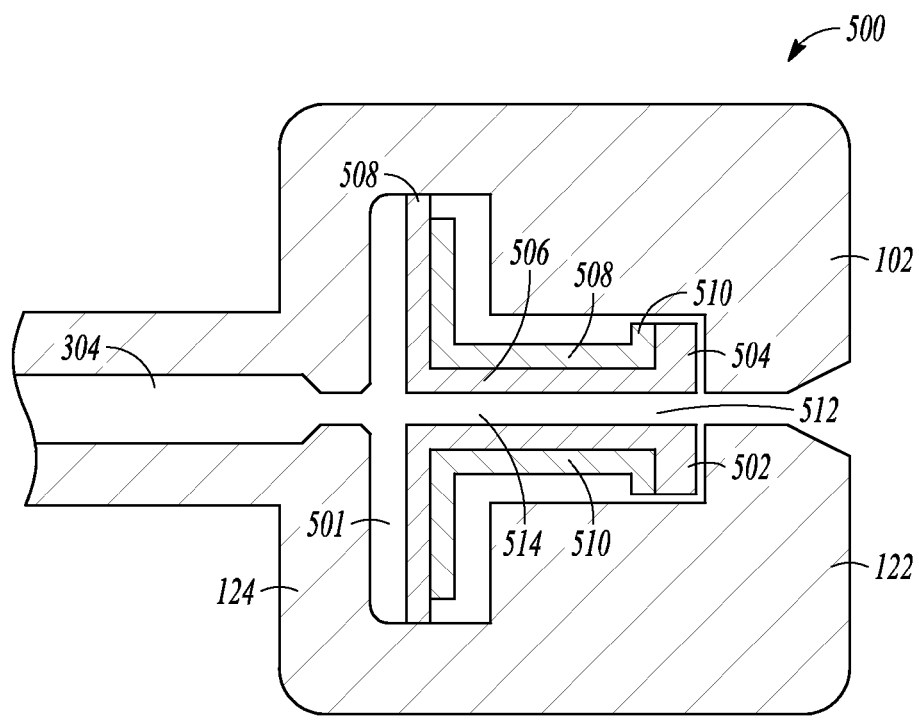
FIG. 5 is a cross-sectional view of another example of a pressure actuated seal assembly including an amplifier.

FIG. 5 shows another example of pressure actuated seal assembly 500. The manifold 102 includes a seal cavity 501 containing the seal element 502 and an amplifier 510. The seal element 502 is coupled with the amplifier 510, for instance, the seal element 502 is over-molded onto the amplifier 510. Molding the seal element 502 on an interior surface of the amplifier 510 allows the seal element lumen 512 and amplifier lumen 514 to automatically align. Assembly of the seal element 502 and amplifier 510 thereby provides a single feature with aligned lumens that automatically guide instruments such as a guide wires through both the seal element and the amplifier.

Referring again to FIG. 5, the seal element 502 includes a seal element ring 504 positioned near a manifold proximal portion 122. A seal element flange 508 of the seal element 502 includes, for instance, a diaphragm extending across the seal cavity 501 near the manifold distal portion 124. A seal element barrel 506 extends between the seal element ring 504 and the seal element flange 508. As shown in FIG. 5, the seal element barrel 506 extends along and is coupled with an interior surface of the amplifier 510. Unitary assembly of the seal element 502 and amplifier 510 automatically aligns the seal element lumen 512 and amplifier lumen 514, as previously discussed above.

In operation, where the manifold lumen 304 receives a pressurized fluid, the fluid presses against the seal element flange and the amplifier 510 positioned adjacent to the seal element flange. The amplifier 510 is constructed of a rigid material, such as a plastic resin, and is pushed toward the seal element ring 504. Pressing of the amplifier 510 against the seal element ring 504 deflects the seal element ring. As the seal element ring 504 is deflected the pliable material of the seal element 502 is compressed toward the manifold proximal portion 122. Compression of the seal element at the seal element ring 504 forces the pliable material in the seal element ring to compress inwardly around the seal element lumen 512. Where an instrument is present within the seal element lumen 512 the seal element ring 504 engages around the instrument and provides a tight seal against the instrument. Where an instrument is absent from the seal element lumen 512 the seal element ring 504 presses inwardly around the seal element lumen 512 and closes the seal element lumen to provide a tight seal that substantially prevents the pressurized fluid in the manifold lumen 304 from moving proximally beyond the manifold proximal portion 122. Stated another way, as the pressure of the working environment within the manifold lumen 304 (and the catheter lumen 306) is increased for a medical procedure, the seal element 502 automatically constricts around the seal element lumen 512 to seal the lumen. Where one or more instruments are present within the seal element lumen 512, the seal element 502 automatically seals around the instruments.

Figure 6:
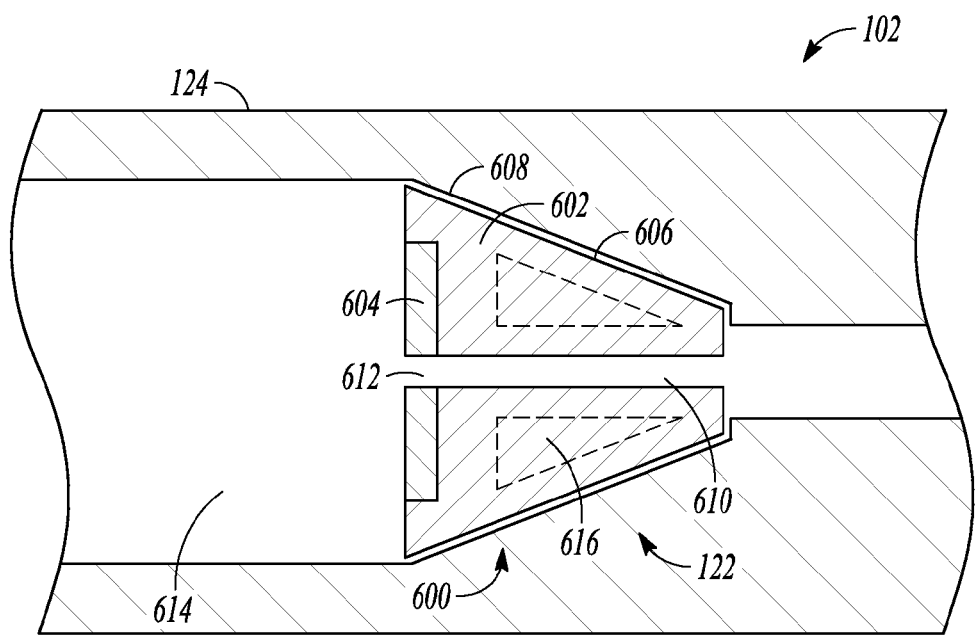
FIG. 6 is a cross-sectional view of yet another example of a pressure actuated seal assembly including an amplifier.

FIG. 6 shows another example of a pressure actuated seal assembly 600 including a seal element 602 and an amplifier 604 as a unitary assembly with the amplifier 604 engaged with the seal element 602. In the example shown in FIG. 6, the amplifier 604 is an amplifier ring formed along a surface of the seal element 602 near the manifold distal portion 124. For instance, the amplifier 604 is over-molded with the pliable material of the seal element 602. In a similar manner to the pressure actuated seal assembly 500 shown in FIG. 5, the seal element lumen 610 and amplifier lumen 612 are automatically aligned with pressure actuated seal assembly 600 because the amplifier 604 is at least partially positioned within the seal element 602. The amplifier lumen 612 is aligned with the seal element lumen 610 without needing guide features formed within the manifold 102 to otherwise align the seal element 602 with the amplifier 604. The seal element 602 extends away from the amplifier 604 toward the manifold proximal portion 122. The seal element 602 shown in FIG. 6 includes a tapered seal surface 606 sized and shaped to correspondingly engage with a tapered seal cavity surface 608 of the seal cavity 601.

In operation, where a pressurized fluid is provided within the catheter, such as the catheter 200 including the manifold lumen 304 and catheter lumen 306, the pressurized fluid engages against the amplifier 604. The rigid amplifier 604 is driven into the seal element 602 and pushes the seal element 602 into tight engagement with the tapered seal cavity surface 608. The tapered seal surface 606 is received along the tapered seal cavity surface 608. Compression of the seal element 602 by the amplifier 604 correspondingly compresses the seal element 602. The tapered seal cavity surface 608 biases the compressed seal element 602 along the tapered seal surface 606 to compress inwardly around the seal element lumen 610. Inward compression of the seal element 602 closes the seal element lumen 610 with the pliable material of the seal element 602. In a similar manner to the amplifier 208 shown in FIGS. 2 and 3 the seal element 602 has a greater distal cross-sectional area near the manifold distal portion 124 compared to the cross-sectional area of the seal element 602 near the manifold proximal portion 122. As the cross-sectional area of the seal element 602 decreases from the manifold distal portion 124 to the manifold proximal portion 122 the force transmitted through the seal element 602 by way of the amplifier 604 is correspondingly multiplied. The multiplied force urges the pliable material of the seal element 602 into the seal element lumen 610 according to the shape of the tapered seal cavity surface 608 and tapered seal surface 606.

In another example shown in FIG. 6, the seal element 602 includes a fluid reservoir 616. The fluid reservoir 616 is filled with a fluid such as saline, silicone and the like. The fluid reservoir 616 and fluid held within the cavity enhances the pliability of the seal element 602 and increases the compressibility of the seal element 602. With a pressurized fluid within the manifold lumen 614 the seal element 602 is more easily compressed to close the seal element lumen 610. While the fluid reservoir 616 is shown in FIG. 6 a seal element fluid reservoir is also an option with the other exemplary seal elements described herein where increased pliability of the seal element 602 is advantageous to increase the compressibility of the seal element 602 and thereby more easily form a tight seal within the seal element lumen. The seal element 602 (as well as other seal elements described herein) is optionally constructed with other materials or configurations. For example, the seal element 602 is constructed with, but not limited to, a sponge, closed cell foam, open cell foam with a sealed skin and the like.

Figure 7:
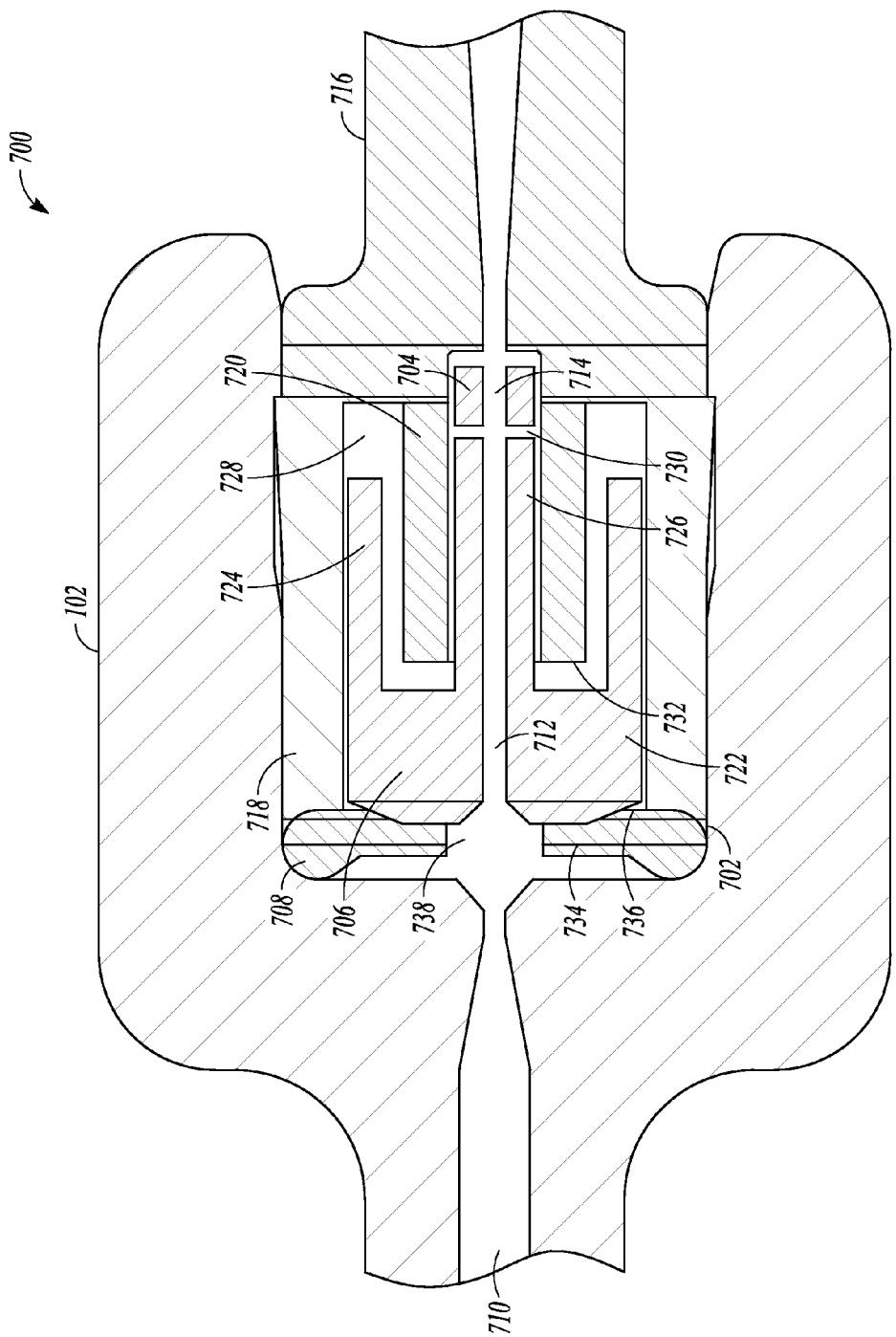
FIG. 7 is a cross-sectional view of one example of a pressure actuated seal assembly including a diaphragm.
Figure 8:
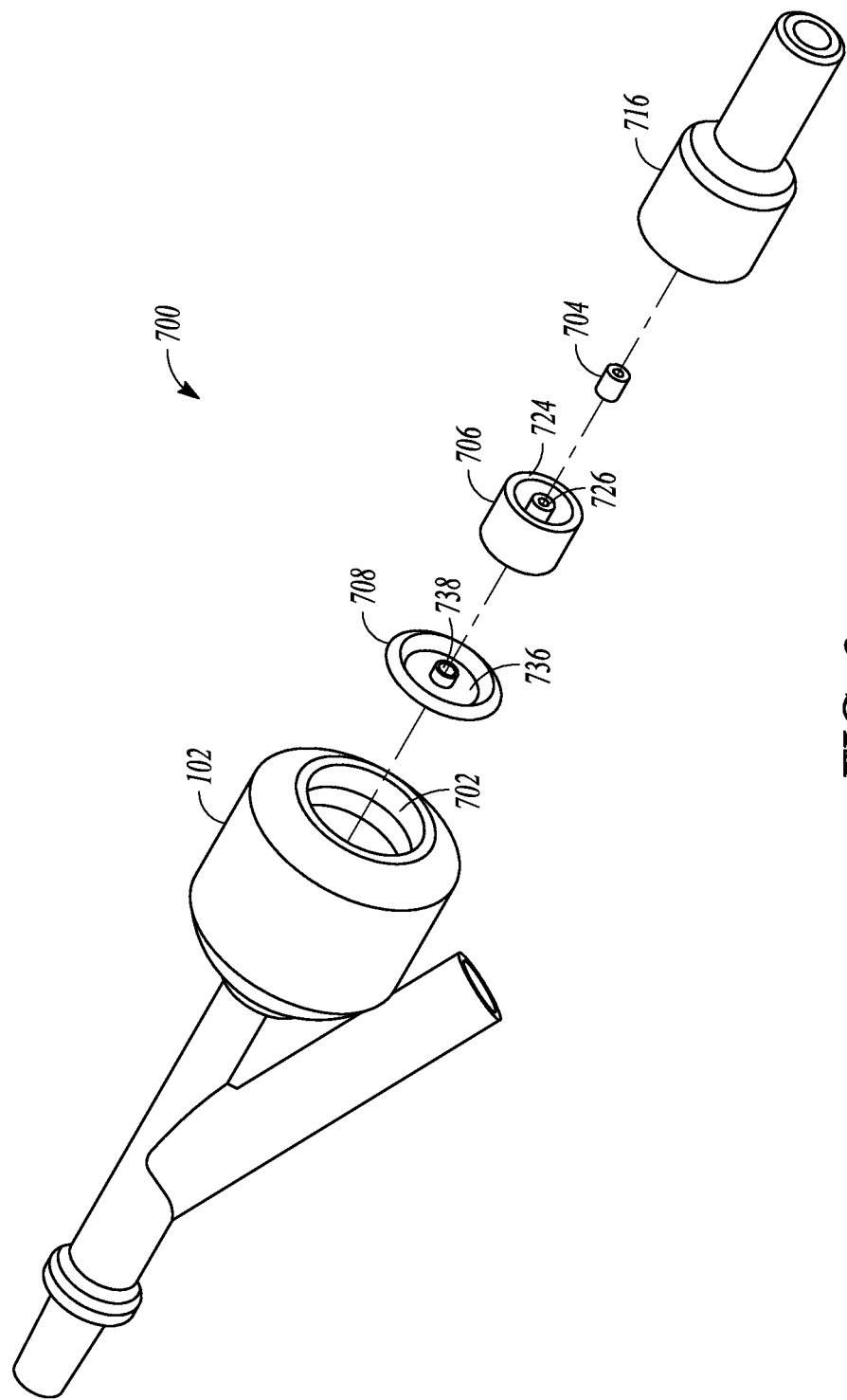
FIG. 8 is an exploded view of the pressure actuated seal assembly shown in FIG. 7.

FIGS. 7 and 8 show another example of pressure actuated seal assembly 700. As described in other examples, the pressure actuated seal assembly 700 is retained within the manifold 102. As shown in FIGS. 7 and 8, the pressure actuated seal assembly 700 is retained within a seal cavity 702 and a diaphragm 708 and a seal element 704. Referring to FIG. 7, an amplifier 706 is interposed in between the diaphragm 708 and the seal element 704, in one example. A series of lumens are in communication within the catheter (e.g., the catheter 200) including the pressure actuated seal assembly 700. For instance, as shown in FIG. 7, the manifold 102 includes a manifold lumen 710. The diaphragm includes a diaphragm lumen 738. The amplifier includes an amplifier lumen 712. The seal element includes a seal element lumen 714. Each of these lumens are in communication with each other and provide a continuous path for the introduction of instruments through the manifold 102 and into the catheter body (e.g., the catheter body 104 shown in FIG. 1).

Referring again to FIGS. 7 and 8, an introducer guide 716 is coupled with the manifold 102 to retain the pressure actuated seal assembly 700 within the manifold. For instance, the introducer guide 716 acts as retainer and is fixedly coupled with the manifold 102. The introducer guide 716 is coupled with the manifold 102 with one or more features including but not limited to a mechanical fitting, an interference fit, adhesives, welding, and the like. As shown in FIG. 7, the introducer guide 716 includes an outer guide barrel 718 coupled with the adjacent manifold 102 and an inner guide barrel 720 extending around the seal element 704 and a portion of the amplifier 706. The amplifier 706 includes an amplifier base 722 interposed between the inner guide barrel 720 and the diaphragm 708. The amplifier 706 further includes in the example shown an amplifier ring 724 extending around the inner guide barrel 720. The amplifier ring 724 is retained within an amplifier ring recess 728 formed between the outer guide barrel 718 and inner guide barrel 720 of the introducer guide 716. An amplifier piston 726 extending from the amplifier base 722 includes at least a portion of the amplifier lumen 712 extending therein. The amplifier piston 726 is shown in FIGS. 7 and 8 and is sized and shaped for reception within the inner guide barrel 720.

Referring to the assembled view shown in FIG. 7, the amplifier 706 is sized and shaped for movable coupling within the introducer guide 716. For instance, the amplifier ring 724 is sized and shaped for movable or slidable coupling within the amplifier ring recess 728 between the outer guide barrel 718 and the inner guide barrel 720 of the introducer guide 716. The amplifier piston 726 is sized and shaped for slidable coupling within the inner guide barrel 720. In one other example, the inner guide barrel 720 snuggly extends around the amplifier piston 726 allowing the amplifier piston 726 to move proximally and distally according to pressure incident on the diaphragm 708 while still providing lateral support to the amplifier 706 to substantially prevent misalignment of the amplifier piston relative to the seal element 704. Stated another way, the introducer guide 716 including the outer guide barrel 718 and the inner guide barrel 720 maintains the amplifier 706 and the amplifier lumen 712 in proper alignment with the diaphragm lumen 738 and the seal element lumen 714. Misalignment of the lumens extending through the manifold 102 is thereby substantially avoided through the guiding function provided by the interfitting between the introducer guide 716 and the amplifier 706.

In operation, where a pressurized fluid is present within the manifold lumen 710 the seal element 704 automatically closes the seal element lumen 714. The pressurized fluid engages against the diaphragm 708 including a first diaphragm surface 734. The second diaphragm surface 736, opposed to the first diaphragm surface 734, correspondingly engages against the amplifier 706. For instance, the second diaphragm surface 736 engages with the amplifier base 722 and pushes the amplifier 706 proximally toward the seal element 704 retained within the amplifier piston recess 730 along with the amplifier piston 726. Proximal movement of the amplifier piston 726 into engagement with the seal element 704 compresses the seal element 704 linearly within the amplifier ring recess 728. As shown in FIG. 7, the seal element 704 is snuggly received within the amplifier piston recess 730 and linear compression of the seal element 704 correspondingly compresses the pliable seal element 704 inwardly around the seal element lumen 714. The amplifier piston recess 730 substantially prevents the seal element 704 from expanding away from the seal element lumen 714. Compression of the seal element 704 closes the seal element lumen 714 to substantially seal the manifold lumen 710, diaphragm lumen 738 and amplifier lumen 706 from outside access through the introducer guide 716. In another example, where one or more instruments is present within the seal element lumen 714, pressing of the amplifier piston 726 on the seal element 704 compresses the seal element 704 on the one or more instruments thereby creating a tight seal around the one or more instruments and sealing lumens 710, 738, and 712 by way of the seal element 704.

In one example, the inner guide barrel 720 includes an inner barrel stop 732 sized and shaped to engage with the amplifier base 722 after the amplifier 706 is moved proximally within the seal cavity 702. The inner barrel stop 732 engages with the amplifier 706 to arrest additional proximal movement of the amplifier and prevent damage to the seal element 704 by over-compression of the seal element 704. Stated another way, the inner barrel stop 732 substantially prevents movement of the amplifier 706 past a specified position within the seal cavity 702 thereby preserving the structural integrity of the seal element 704 over the operational lifetime of the pressure actuated seal assembly 700.

When the pressurized fluid is no longer present within the manifold lumen 710 or is no longer pressurized the seal element 704 is free to relax and resume an undeformed state with the seal element lumen 714 open to freely pass fluids, instruments, guide wires and the like therethrough and provide access to the amplifier lumen 712, diaphragm lumen 738, manifold lumen 710, and the catheter lumen (e.g., catheter lumen 306 shown in FIG. 3). Optionally, the amplifier 706 is coupled along the second diaphragm surface 736, for instance by adhesives, welds, and the like. Removal of the pressure within the manifold lumen 710 allows the pliable diaphragm 708 to resume a relaxed position shown in FIG. 7. Where the amplifier 706 is coupled with the diaphragm 708, relaxation of the diaphragm returns it to its relaxed position and correspondingly pulls the amplifier 706 out of compressing engagement with the seal element 704 thereby allowing the seal element 704 to resume a relaxed state with the seal element lumen 714 open to allow the passage of fluids, instruments and the like.

In the pressure actuated seal assembly 700 described above the seal element 704 and diaphragm 708 are constructed with, but not limited to, pliable materials capable of deflecting and compressing according to a pressurized fluid within at least the manifold lumen 710. The diaphragm 708 and seal element 704 include, for instance, pliable polymers including silicon, butyl rubber and the like. The amplifier 706, in at least one example, is constructed with a more rigid material, including but not limited to, resins such as polycarbonate, DELRIN plastic (a trademarked product of DuPont), polyvinyl chloride and the like.

In one example, the diaphragm 708 is retained within the seal cavity 702 between the introducer guide 716 and the inner surface of the seal cavity 702 within the manifold 102. For instance, as shown in FIG. 7 the introducer guide 716 including the outer guide barrel 718 is engaged with a portion of the diaphragm 708 thereby squeezing the diaphragm 708 between the introducer guide 716 and the manifold 102. The diaphragm 708 is therefore held in a position within the seal cavity 702 by the tight engagement between the introducer guide 716 and the manifold 102. In another example, the diaphragm 708 is coupled to the manifold 102 with a feature, including but not limited to, a mechanical interfitting, adhesives, welds, and the like. Retention of the diaphragm 708 in the orientation shown in FIG. 7 substantially prevents the movement of pressurized fluids around the diaphragm 708 and facilitates the transmission of forced from the diaphragm 708 to the seal element 704 to achieve closure of the seal element lumen 714.

Figure 9:
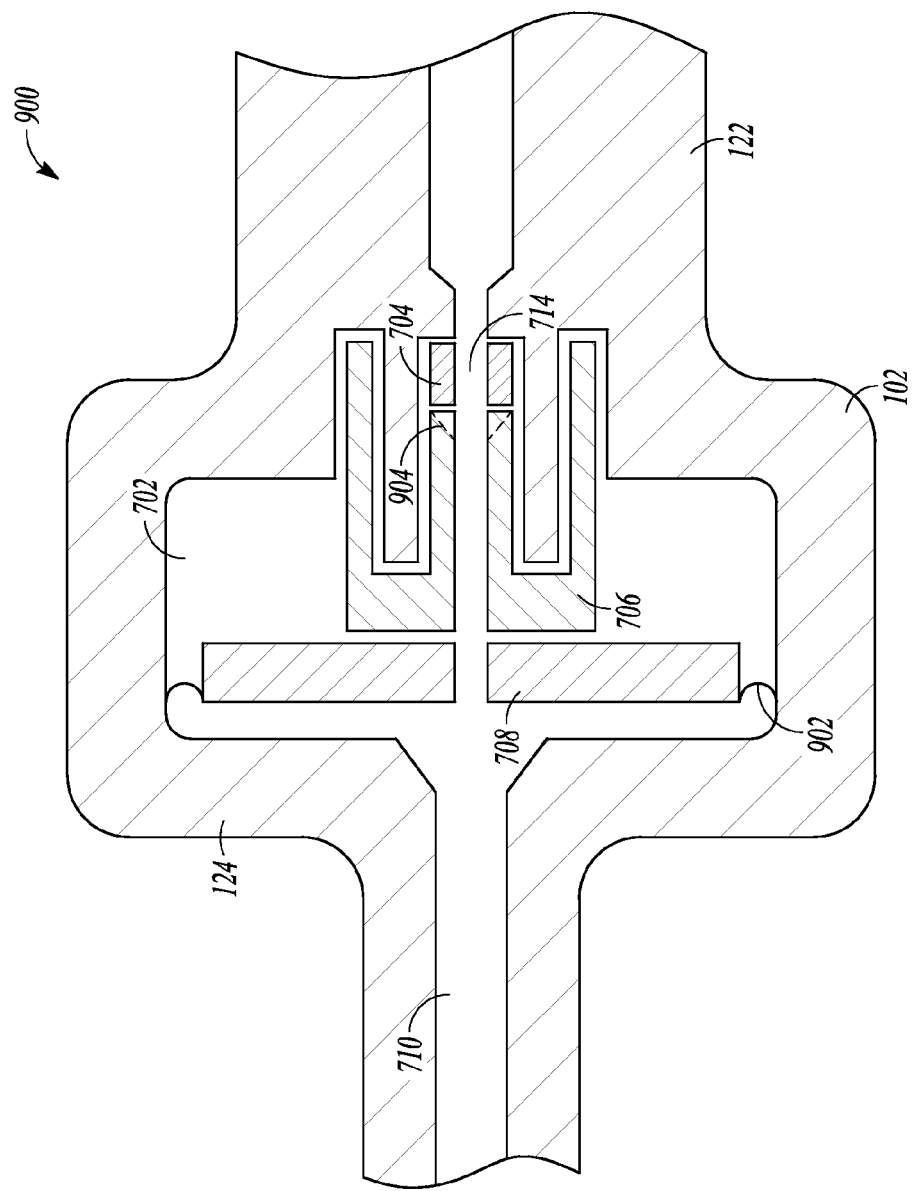
FIG. 9 is an exploded view of one example of a pressure actuated seal assembly including a diaphragm and an amplifier.

Referring now to FIG. 9, another example of a pressure actuated seal assembly 900 is shown. The pressure actuated seal assembly 900 is similar in at least some regards to the pressure actuated seal assembly 700 shown in FIGS. 7 and 8. For example, the pressure actuated seal assembly 900 includes the seal element 704 positioned adjacent to the amplifier 706, and the amplifier 706 is positioned adjacent to the diaphragm 708 within the seal cavity 702. The pressure actuated seal assembly 900 includes as an option a rolling diaphragm 902 extending from the diaphragm 708 to an interior surface of the manifold 102 forming the seal cavity 702. As with the diaphragm 708 described above and shown in FIGS. 7 and 8, the diaphragm 708 including the rolling diaphragm 902 substantially prevents the movement of pressurized fluids around the diaphragm 708 and ensures engagement of the pressurized fluids along the surfaces of the diaphragm 708 correspondingly moves the diaphragm into engagement with the amplifier 706 to compress the seal elements 704. The amplifier 706 shown in FIG. 9 includes an optional tapered guide surface 904. The tapered guide surface 904 is shown in phantom lines in FIG. 9 and tapers from the manifold proximal portion 122 towards the manifold distal portion 124. The amplifier tapered guide surface 904 provides a tapered surface sized and shaped to guide an instrument, such as a guide wire, from the seal element lumen 714 to the amplifier 706. The tapered guide surface, such as the tapered guide surface 904, shown in FIG. 9 is equally applicable to any of the pressure actuated seal assemblies discussed herein to facilitate the movement of an instrument through the pressure actuated seal assemblies during loading of the instrument into the manifold 102.

Figure 10:
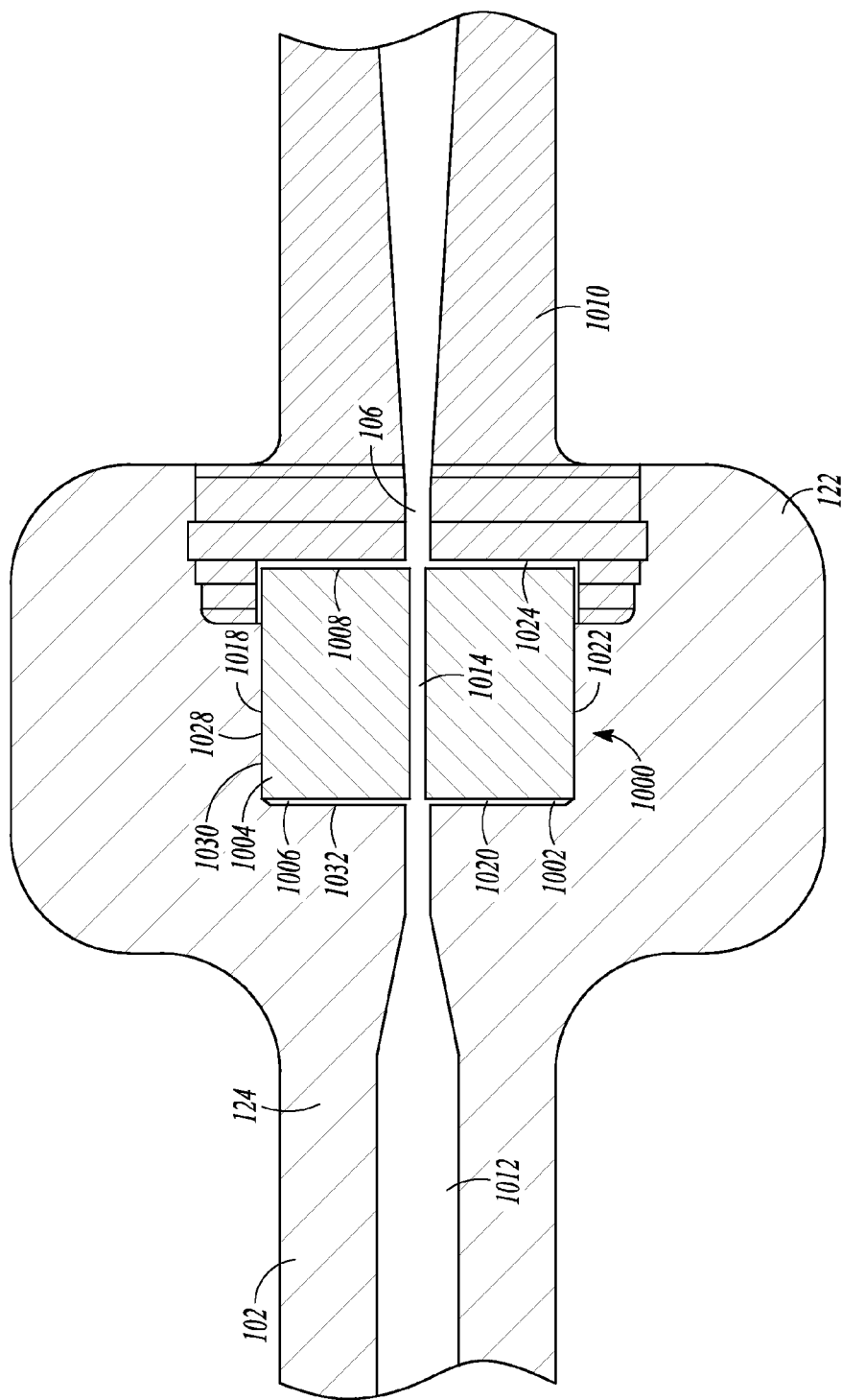
FIG. 10 is a cross-sectional view of one example of a pressure actuated seal assembly including a pliable seal element.

FIG. 10 shows another example of a pressure actuated seal assembly 1000. The pressure actuated seal assembly includes a seal element 1004 contained within an elongate seal cavity 1002 of the manifold 102. As shown in FIG. 10, the seal element 1004 fills a large portion of the seal cavity 1002. The elongate seal cavity 1002 includes a seal cavity perimeter 1022 extending between a seal cavity proximal end 1024 and a seal cavity distal end 1020. The elongate seal cavity 1002 is larger than the manifold lumen 1012 of the manifold 102. As described in further detail below, the elongate seal cavity 1002 provides a large volume for reception of the seal element 1004 having a corresponding large volume elongated shape. The seal element is able to readily deflect axially toward the seal cavity distal end 1020 (and compress all of the seal material therebetween) when under pressure and thereby inwardly compress and close a seal element lumen 1014.

As previously described with respect to other seal elements, the seal element 1004 is constructed with a pliable material configured to axially compress under pressure and correspondingly inwardly compress around the seal element lumen 1014. As shown in FIG. 10, the seal element 1002 has a cylindrical shape extending around the seal element lumen 1014. The seal element 1004 includes a first seal face 1006 directed distally toward the manifold distal portion 124 and a second seal face 1008 directed toward a manifold proximal portion 122. In one example, the seal element 1004 is retained within the seal cavity 1002 with an introducer guide 1010 acting as a retainer. The introducer guide 1010 is coupled with the manifold 102 (e.g., through snap fitting, threading and the like) and encloses the seal cavity 1002 thereby retaining the seal element 1004 therein. The manifold inner surface 1018 defines the seal cavity 1002 with the seal cavity perimeter 1022 and ensures the seal element lumen 1014 of the seal element 1004 is aligned with an introducer lumen 1016 of the introducer guide 1010 and the manifold lumen 1012 within the manifold 102. That is to say a seal element perimeter 1028 is substantially identical to the seal cavity perimeter 1022 and thereby aligns the seal element lumen 1014 with the manifold lumen 1012. As will be described below, a minimal gap 1030 is formed between the seal cavity perimeter 1022 and the seal element perimeter 1028 to facilitate axial deflection of the seal element 1004.

In operation, where a pressurized fluid is present within the manifold lumen 1012, the seal element 1004 is engaged by the fluid across the first seal face 1006 and compresses to automatically seal the seal element lumen 1014. As shown in FIG. 10, the first seal face 1006 is, in one option, spaced a small distance from the distal end 1020 of the seal cavity 1002 to facilitate engagement of the fluid along the first seal face 1006. Stated another way, as shown in FIG. 10 a slit 1032 is formed between the first seal face 1006 positioned immediately adjacent to the distal seal cavity end 1020 to ensure pressurized fluid is directed across the first seal face 1006.

The pressurized fluid engages with the seal element 1004 along the first seal face 1006 and presses the seal element proximally toward the manifold proximal portion 122. Because of the proximal compression of the seal element 1004 the seal element deforms and compresses inwardly around the seal element lumen 1014 thereby closing the seal element lumen. In another example, where an instrument (or instruments), such as a guide wire, is positioned within the seal element lumen 1014 application of a pressurized fluid along the first seal face 1006 presses on the seal element 1004 and compresses the seal element 1004 around the seal element lumen 1014 to seal the seal element 1004 around the instrument therein. The large pliable seal element 1004 under the influence of a pressurized fluid is thereby able to close the seal element lumen 1014 with or without an instrument in the lumen. Optionally, the seal element 1004 closes around instruments and closes the lumen 1014 under high pressures or flow rates (e.g., 100 psi or greater). At lower pressures (e.g., 6 psi), the seal element lumen 1014 remains open to allow for purging of air from the manifold 102 and a catheter coupled with the manifold 102.

Referring again to the first seal face 1006 (shown in FIG. 10), the first seal face 1006 acts as an amplifier to facilitate the deflection and generate a tight seal in the seal element 1004. That is to say, the large surface area of the first seal face 1006 (relative to the area of the seal element lumen 1014 or the manifold lumen 1012) exposed by the slit 1032 provides an amplifier surface that transmits compressive force generated along its entire surface through engagement with pressurized fluid in the manifold lumen 1012. Stated another way, by exposing a large surface area of the seal element 1004 (e.g., the first seal face 1006) to the pressurized fluid all of the pliable material beneath the face 1006 is compressed. In contrast, where a smaller seal face is exposed (relative to the face 1006 exposed with the slit 1032) only the material beneath the face is compressed. In other words, by increasing the size of the seal element 1004 and correspondingly increasing the size of the first seal face 1006 a large quantity of pliable seal material is squeezed outward and inward to readily close the seal element lumen 1014 and any gaps 1030 between the seal element perimeter 1028 and the surfaces defining the seal element cavity 1002 (e.g, the seal cavity perimeter 1028).

The pressure actuated seal assembly 1000 closes the seal element lumen 1014 without an amplifier, such as a separate amplifier 208 shown in FIG. 2. The pliable material of the seal element 1004 including, but not limited to, silicone, butyl rubber and the like deflects under the pressure from the fluid. The pliable material of the seal element 1004 along with the relatively large size of the seal element at the first seal face 1006 compared to the material of the seal element surrounding the seal element lumen 1014 enhances the deflection of the seal element 1004. The enhanced deformation of the seal element under the influence of the pressurized fluid permits removal of the amplifier.

Furthermore, in examples where the seal element is positioned around an instrument (e.g., a guide wire and the like) the gap between the seal element 1004 and the instrument in the seal element lumen 1014 is small. A fluid flow into the catheter will have a difficult time leaking through this gap and the pressure builds across the seal element 1004. Correspondingly, tighter gaps between the seal element and the instrument seal quickly and easily. Further the durometer of the seal 1004 is important. A readily deformable low durometer seal rapidly deforms under pressure and correspondingly quickly and tightly seals the seal element lumen 1014. Moreover, the surface area and volume of the seal affect the quality of the seal and the speed a seal is formed. Seals with relatively large surface areas and volumes relative to the seal element lumen 1014 deform quickly and easily. Similarly, a thick seal element 1004 with a long seal element lumen 1014 has a correspondingly long and difficult to pass gap between the instrument and the seal element. A longer gap path allows more pressure to build at the seal element 1004 and thereby deforms the seal element to close the seal element lumen 1014. Further still, greater flow rates (e.g., under pressure) build pressure more quickly and readily deform the seal element 1004 to create a tighter seal relative to seals created with lower flow rates. Infusate fluids with high viscosity also build pressure at the seal element 1004 because of the difficulty in moving viscous fluids through the seal element 1004 prior to deformation. Based on these specifications, the seal 1004 (or the seal examples described herein) are tailored via mechanical properties, dimensions, and tolerances to achieve a successful seal during periods of infusion.

Figure 11:
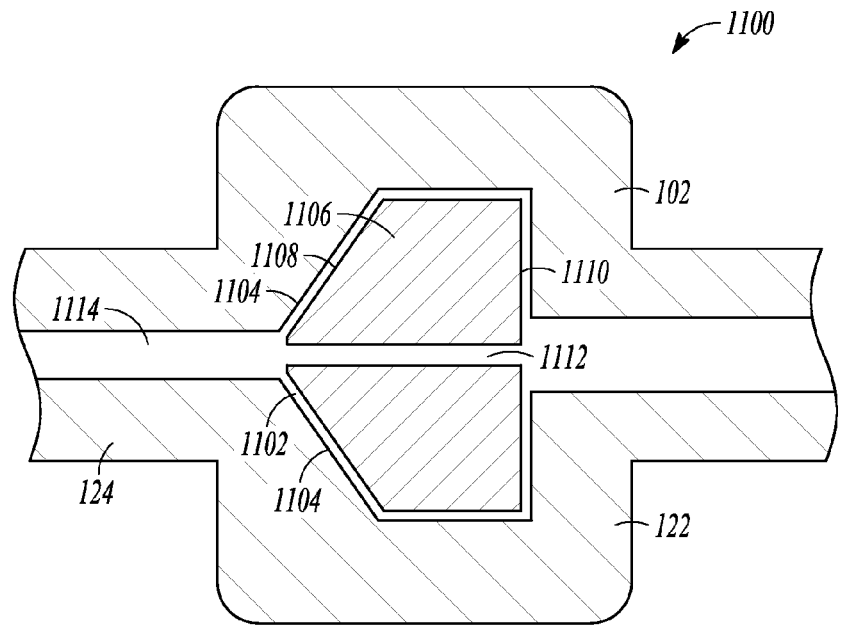
FIG. 11 is a cross-sectional view of another example of a pressure actuated seal assembly having a pliable seal element including a tapered seal element face.

Referring now to FIG. 11, another example of a pressure actuated seal assembly 1100 is shown including a seal element 1106 having a tapered seal face 1108. As in some previous examples, the seal element 1106 is positioned within a seal cavity 1102 of a manifold 102. As shown in FIG. 11, the seal cavity 1102 includes a tapered seal cavity surface 1104 sized and shaped to correspond to the tapered seal face 1108 of the seal element 1106. The seal element 1106 further includes a proximal seal face 1110 positioned near the manifold proximal portion 122. The tapered seal face 1108 of the seal element 1106 is shown in FIG. 11 on a distal side of the seal element near the manifold distal portion 124. In another option, the tapered seal face 1108 is on the proximal seal face 1110 near the manifold proximal portion 122. The seal element 1106 is positioned within the seal cavity 1102 so the seal element lumen 1112 is substantially aligned with a manifold lumen 1114, as shown in FIG. 11.

In operation, where a pressurized fluid is present within the manifold lumen 1114 the pressurized fluid engages with the tapered seal face 1108 of the seal element 1106. The tapered seal face 1108 provides a larger surface area for the pressurized fluid to engage against thereby enhancing the force applied to the seal element 1106 and correspondingly enhancing the deflection of the seal element 1106 and its inward compression around the seal element lumen 1112. The pressurized fluid engaged along the tapered seal face 1108 presses the seal element 1106 proximally, and the seal cavity 1102 substantially prevents expansion of the seal element 1106 outwardly. Instead, proximal compression of the seal element 1106 forces the seal element 1106 to compress inwardly around the seal element lumen 1112 thereby closing the seal element lumen 1112 and providing a tight seal that substantially prevents the passage of the pressurized fluid past the seal element 1106. As in previous examples, where an instrument, such as a guide wire, is present within the seal element lumen 1112 application of the pressurized fluid along the tapered seal face 1108 compresses the seal element 1106 around the instrument within the seal element lumen thereby closing the seal element 1106 around the instrument and providing a tight seal that substantially prevents the passage of fluids beyond the seal element 1106.

Figure 12:
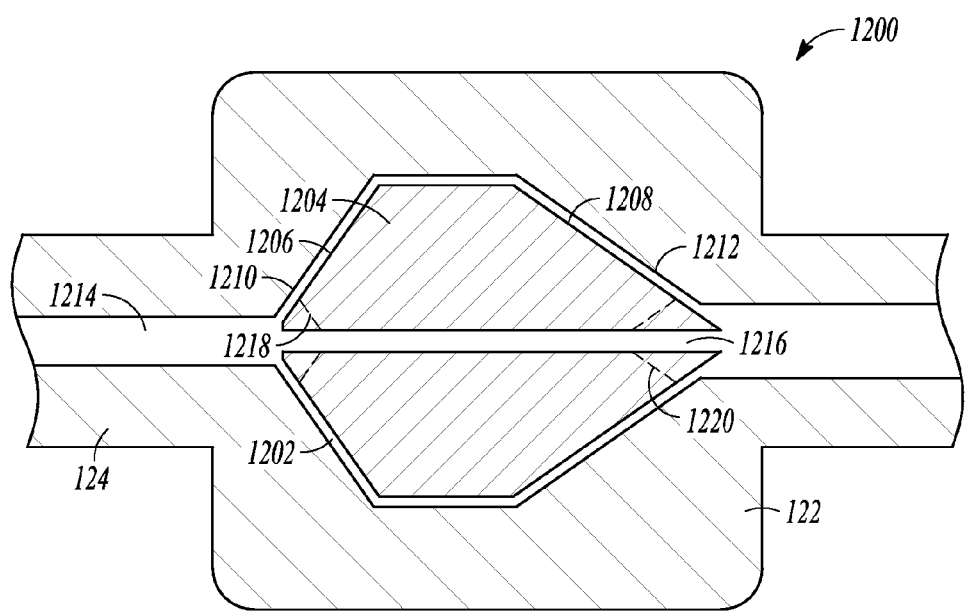
FIG. 12 is a cross-sectional view of yet another example of a pressure actuated seal assembly having a pliable seal element and including a tapered seal element faces on first and second sides of the seal element.

FIG. 12 shows yet another example of a pressure actuated seal assembly 1200. The pressure actuated seal assembly 1200 includes a seal element 1204 positioned within a seal cavity 1202. As shown in FIG. 12, the seal element 1204 includes a distal tapered seal face 1206 and a proximal tapered seal face 1208. The tapered seal faces 1206, 1208 are sized and shaped for reception within the seal cavity 1202 having a corresponding distal tapered cavity surface 1210 and a proximal tapered cavity surface 1212. The tapered cavity surfaces 1210, 1212 are configured in substantially the same shape as the tapered seal faces 1206, 1208 of the seal element 1204. In another example, at least one of the tapered seal faces and tapered cavity surfaces are tapered at different angles relative to the corresponding seal face or cavity surface. One of the seal cavity 1202 or the seal element 1204 thereby has a distinct shape from the other of the seal cavity and the seal element. A manifold lumen 1214 extends through the manifold 102 and is in substantial alignment with the seal element lumen 1216 extending through the seal element 1204. Optionally, the seal element 1204 includes at least one guide such, as a proximal instrument guide 1218 and a distal instrument guide 1220 (each of which is shown in phantom lines). The proximal and distal instrument guides 1218, 1220 facilitate passage of an instrument, for instance a guide wire, through the seal element lumen 1216 and into the manifold lumen 1214. In another example, the distal instrument guide 1220 facilitates movement of an instrument proximally, such as a front loaded guide wire, through the manifold lumen 1214, into the seal element 1204 and proximally out of the seal element 1204.

In operation, pressurized fluid within the manifold lumen 1214 applies a force across the distal tapered seal face 1206 and forces the seal element 1204 proximally within the seal cavity 1202. As described in the example shown in FIG. 11, the distal tapered seal face 1206 provides enhanced surface area and provides a larger surface for the pressurized fluid to act upon the seal element 1204. The seal element 1204 thereby experiences greater forces and corresponding greater deflection as the seal element 1204 is urged proximally. The proximal tapered seal face 1208 on the seal element is engaged against the proximal tapered cavity surface 1212 and guides compression of the seal element 1204 inwardly around the seal element lumen 1216. The engagement between the proximal tapered seal face 1208 and the proximal tapered cavity surface 1212 thereby acts as an amplifier substantially directing the seal element 1204 to compress inwardly as opposed to outwardly and enhances the inward deformation of the seal element around the seal element lumen 1216. Compression of the seal element 1204 inwardly closes the seal element lumen 1216 with or without an instrument present to substantially prevent passage of the pressurized fluid beyond the seal element 1204. When the fluid within the manifold lumen 1214 is no longer under pressure, the natural elasticity of the seal element 1204 allows the seal element to resume its undeformed state thereby allowing the seal element 1204 to expand and open the seal element lumen 1216 for passage of fluids, instruments and the like.

Figure 13:
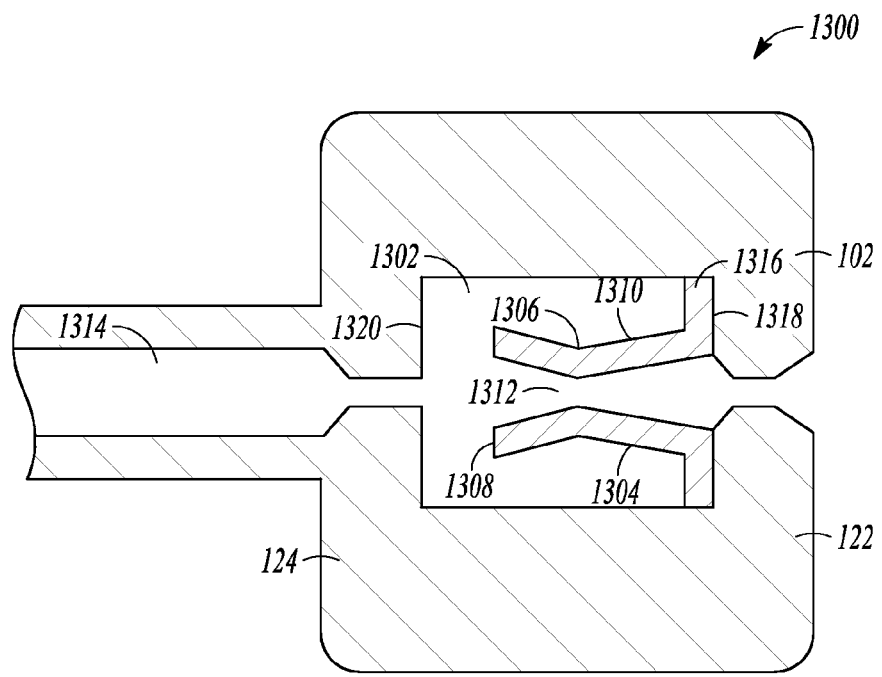
FIG. 13 is a cross-sectional view of still another example of a pressure actuated seal assembly having a pliable seal element including a deformable lip.

Another example of a pressure actuated seal assembly 1300 is shown in FIG. 13, and includes a seal element 1304 having a deformable lip 1306. The seal element 1304 is disposed within the seal cavity 1302 of the manifold 102. The deformable lip 1306 of the seal element 1304 includes, in one example, a distal tapered lip portion 1308 and proximal tapered lip portion 1310. The tapered lip portions 1308, 1310 are sized and shaped to guide an instrument fed through the manifold 102 proximally or distally. The tapered lip portions 1308, 1310 thereby guide an instrument into the seal element lumen 1312 of the seal element 1304. As shown in FIG. 13, the seal element lumen 1312 of the seal element 1304 is substantially aligned with the manifold lumen 1314 of the manifold 102. The seal base 1316 is coupled across a seal cavity proximal surface 1318 and positions the seal element 1304 within the seal cavity 1302 to align the seal element lumen 1312 with the manifold lumen 1314. Optionally, the seal element 1304 is spaced from the seal cavity distal surface 1320. Spacing of the seal element 1304 from the seal cavity distal surface 1320 allows for fluid, including pressurized fluid, within the manifold lumen 1314 to move around the seal element 1304. Pressurized fluid surrounding the exterior of the deformable lip 1306 forces the deformable lip 1306 to compress inwardly thereby closing the seal element lumen 1312, as described further below.

In operation, a pressurized fluid present within the manifold lumen 1314 enters the seal cavity 1302. The pressurized fluid at least partially surrounds the exterior of the deformable lip 1306 of the seal element 1304. The pressurized fluid compresses the deformable lip 1306 inwardly around the seal element lumen 1312. Compression of the deformable lip 1306 around the seal element lumen 1312 closes the seal element lumen to substantially prevent the passage of the pressurized fluid beyond the seal element 1304. In another example, where an instrument is present within the seal element lumen 1312 compression of the deformable lip 1406 around the instrument forces the deformable lip 1306 to tightly engage around the instrument and thereby create a seal that substantially prevents the passage of pressurized fluids between the instrument and the deformable lip 1306. The seal element 1304 including the deformable lip 1306 is constructed with a pliable material including, but not limited to, butyl rubber, silicone and the like. The deformable lip 1306 is constructed with the pliable material to ensure rapid deflection of the deformable lip and inward compression around the seal element lumen 1312 to provide a tight seal through the manifold 102. In another example, at least a portion of the deformable lip 1306 is coupled with another portion of the surfaces defining the seal cavity 1302. That is to say a distal portion of the deformable lip 1306 is coupled with a distal portion of the seal cavity 1302. In such an example, passages through the deformable lip 1306, for instance, from the seal element lumen 1312 to the exterior of the deformable lip 1306 allow the transmission of pressurized fluid out of the seal element lumen and into the area surrounding the deformable lip 1306. The deformable lip 1306 is thereby engaged by the pressurized fluid on the exterior surfaces of the seal element

1304 to deflect the deformable lip 1306 of the seal element to close the seal element lumen 1312.

Figure 14:
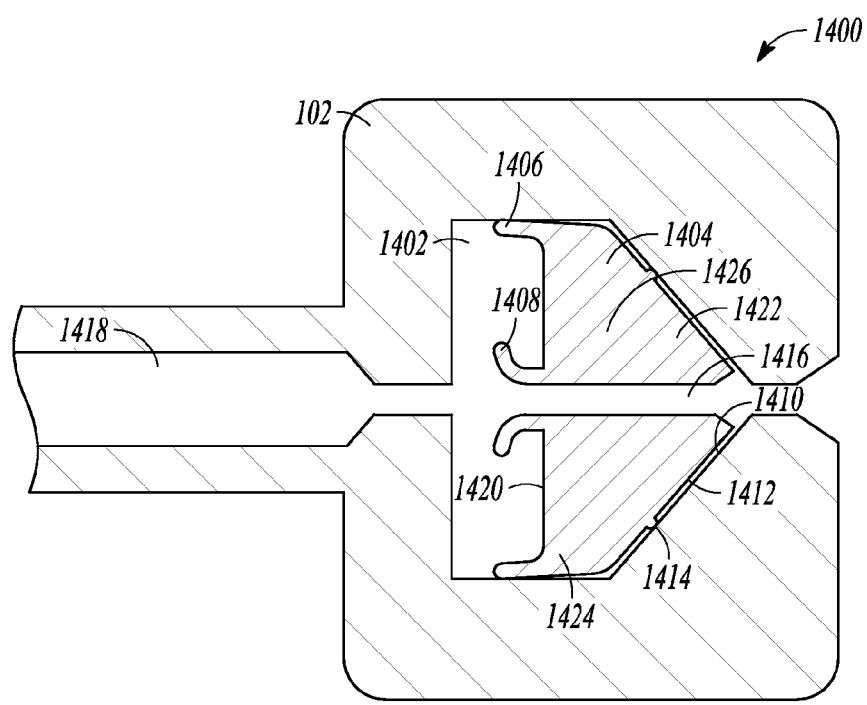
FIG. 14 is a cross-sectional view of a further example of a pressure actuated seal assembly having a pliable seal element with a deformable lip and a tapered seal element face

Referring now to FIG. 14, still another example of a pressure actuated seal assembly 1400 is shown. As in previous examples, the pressure actuated seal assembly 1400 includes a seal element 1404 disposed within a seal cavity 1402 of the manifold 102. The seal element 1404 includes an exterior lip portion 1406. The exterior lip portion 1406 is near a seal element distal portion 1420 and seal element exterior portion 1424. The exterior lip portion 1406 is sized and shaped to engage with the surface defining the seal cavity 1402. The seal element 1404 further includes an interior lip portion 1408 extending from the seal element distal portion 1420 near the seal element interior portion 1426 and the seal element lumen 1416. As further shown in FIG. 14, the seal element 1404 further includes a tapered seal element surface 1412 sized and shaped for engagement with the tapered cavity surface 1410. In yet another example, the seal element 1404 includes a biasing projection 1414 along the tapered seal element surface 1412. The biasing projection 1414 is sized and shaped to ensure the seal element 1304 disengages from the tapered cavity surface 1410 after fluid within the manifold lumen 1418 is no longer pressurized to allow the seal element 1404 to resume a relaxed configuration where the seal element lumen 1416 is capable of passing instruments and fluids.

In operation, where a pressurized fluid is present within the manifold lumen 1418 the pressurized fluid engages with the seal element 1404. The pressurized fluid engages against the exterior lip portion 1406 and deflects the lip portion outwardly to seal the exterior lip portion along the surfaces defining the seal cavity 1402 and substantially prevent passage of pressurized fluids around the seal element 1404. The pressurized fluid also engages with the interior lip portion 1408 and deflects the interior lip portion inwardly. Deformation of the interior lip portion 1408 inwardly assists in sealing the seal element lumen 1416 as the interior lip portion 1408 compresses around the seal element lumen 1416. The pressurized fluid further compresses the seal element 1404 proximally into the manifold 102 thereby forcing the tapered seal element surface 1412 into engagement with the tapered cavity surface 1410. The tapered seal element surface 1412 cooperates with the tapered cavity surface 1410 to exert an inward compressive force on the seal element 1404 toward the seal element lumen 1416. The pliable material in the seal element 1404 is pressed inwardly into the seal element lumen 1416 creating a tight seal and substantially preventing the passage of the pressurized fluid through the seal element 1404. Stated another way, the tapered seal element surface 1412 and tapered cavity surface 1410 cooperate and act as an amplifier to enhance the deformation of the seal element 1404 inwardly toward the seal element lumen 1416. Once the fluid is no longer pressurized, the seal element 1404 resumes a relaxed orientation because of its natural elasticity. In the relaxed orientation the seal element lumen 1416 is open and an instrument may pass through the seal element. The biasing projections 1414 shown in FIG. 14 provide a biasing force to the seal element 1404 and push the seal element 1404 out of engagement with the tapered cavity surface 1410. The biasing projections 1414 thereby prevent the seal element 1404 from interlocking with the tapered cavity surface 1410 and remaining in a compressed orientation after the fluid is no longer pressurized.

Figure 15:
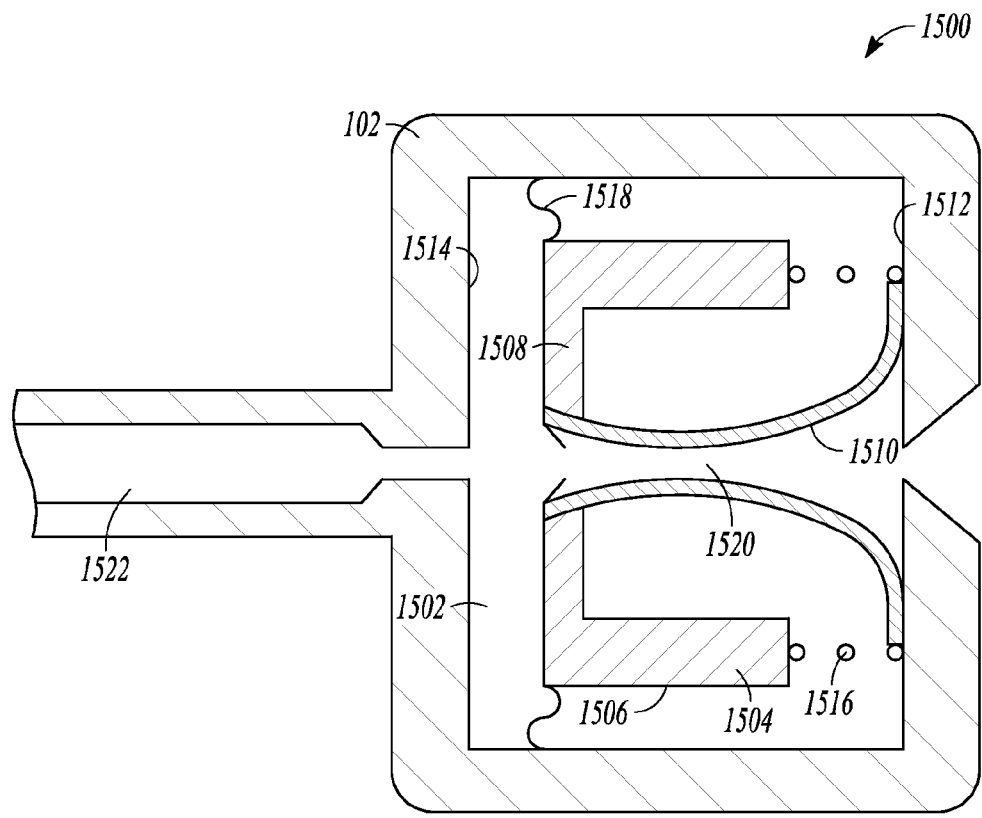
FIG. 15 is a cross-sectional view of one example of a pressure actuated seal assembly having a pliable seal element coupled with a plunger.

FIG. 15 shows another example of a pressure actuated seal assembly 1500. The pressure actuated seal assembly 1500 includes a plunger 1504 and a seal element 1510 positioned within a seal cavity 1502. The plunger 1504 is movably coupled within the seal cavity 1502 and is moved proximally and distally to seal and unseal the seal element 1510, respectively. In one example, the plunger 1504 includes a plunger barrel 1506 and plunger face 1508. The plunger barrel 1506 is coupled with a biasing member 1516 and the biasing member 1516 is coupled between the plunger and a proximal seal cavity portion 1512. The biasing member 1516 (e.g., a spring, elastomer or the like) is configured to bias the plunger 1504 away from the proximal seal cavity portion 1512 toward the distal seal cavity portion 1514 near the manifold lumen 1522. The seal element 1510 is coupled between the plunger face 1508 and the proximal seal cavity portion 1512. The plunger 1504 is sized and shaped to fit within the seal cavity 1502, and aligns a seal element lumen 1520 extending through the seal element 1510 with the manifold lumen 1522 extending through the manifold 102. Alignment of the seal element lumen 1520 with the manifold lumen 1522 assists in ensuring that instruments, including guide wires, are reliably fed through the lumens from the manifold 102 to the catheter body 104 (or from the catheter body 104 to the manifold 102). In one example, the pressure actuated seal assembly 1500 includes a rolling diaphragm 1518 extending from the manifold 102 through the seal cavity 1502 to the plunger face 1508. As described in previous examples, the rolling diaphragm 1518 substantially prevents passage of pressurized fluids around the plunger 1504 while allowing the plunger 1504 to move within the seal cavity 1502 to create a seal with the seal element 1510. The seal element 1510 is constructed with a pliable material including but not limited to butyl rubber, silicone, and the like. The pliable material of the seal element 1510 cooperates with movement of the plunger 1504 to deflect the seal element 1510 around the seal element lumen 1520.

In operation, where a pressurized fluid is present within the manifold lumen 1522 the pressurized fluid engages against the plunger 1504 and moves the plunger proximally toward the proximal seal cavity portion 1512. The pressurized fluid incident on the plunger face 1508 provides sufficient pressure against the plunger 1504 to overcome the biasing force of the biasing member 1516 allowing the plunger 1504 to move proximally within the seal cavity 1502. Movement of the plunger 1504 is transmitted to the seal element 1510. The pliable material of the seal element 1510 allows the seal element 1510 to deflect inwardly upon movement of the plunger 1504. As the plunger 1504 moves proximally the seal element 1510 deflects inwardly and closes the seal element lumen 1520. Where an instrument is present within the seal element lumen 1520 the deflecting pliable material of the seal element 1510 closes around the instrument within the seal element lumen and seals around the instrument preventing the passage of pressurized fluid through past the seal element 1510. Once the fluid within the manifold lumen 1522 and the seal cavity 1502 is no longer pressurized the plunger 1504 is moved distally toward the distal seal cavity portion 1514 by the biasing member 1516. As the plunger 1504 moves distally the seal element 1510 coupled between the plunger 1504 and the proximal seal cavity portion 1512 is pulled apart opening the seal element 1520. As the seal element 1510 is opened fluid may pass through the seal element lumen 1520. Similarly, an instrument may pass through the seal element lumen 1520 after the plunger 1504 is moved distally and the seal element 1510 relaxes to the orientation shown in FIG. 15.

Optionally, with the pressure actuated seal assembly 1500 and any of the pressure actuated seal assemblies described herein, an introducer is fed through the seal element lumen 1520 prior to closure of the seal element 1510 by the pressurized fluid. The introducer includes a lumen capable of passing an instrument, such as a guide wire. Once the seal element 1510 is sealed around the introducer (e.g., because of pressurized fluid within the manifold lumen) the instrument is fed through the lumen of the introducer as desired by the operator. The introducer thereby facilitates feeding of the instrument through the catheter body while a pressurized fluid is present within the catheter body and the seal element 1510 is compressed inwardly into the seal element lumen 1520.

Figure 16:
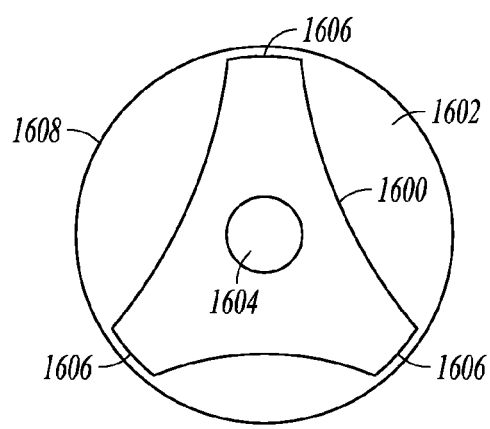
FIG. 16 is a top view of one example of the slider shown in FIG. 15.

FIG. 16 shows another example of a plunger 1600 sized and shaped for use with the pressure actuated seal assembly 1500. The plunger 1600 is disposed within a seal cavity 1602 and the plunger is sized and shaped to move proximally and distally (relatively into and out of the page) according to the presence or absence of pressurized fluid within the manifold lumen 1522. Similarly to the seal element lumen 1520 extending through the plunger 1504 in FIG. 15 a seal element lumen 1604 extends through the plunger 1600 in FIG. 16. A seal element, such as seal element 1510, is coupled with the plunger 1600 and coupled with a seal cavity portion, (e.g., the proximal seal cavity portion 1512 shown in FIG. 10). Referring again to FIG. 16, the plunger 1600 is shown with one or more plunger edges 1606 in close proximity to the seal cavity wall 1608. The plunger edges 1606, in one example, minimize contact between the plunger 1600 and the seal cavity wall 1608 thereby freely allowing the plunger 1600 to move proximally and distally within the seal cavity 1602 without interference with the seal cavity wall 1608. The plunger 1600 is thereby able freely move proximally and distally without the plunger 1600 snagging along the seal cavity wall 1608 and frustrating the ability of the seal element 1510 to open or close. In another example, the plunger edges 1606 are points sized and shaped to ride along the seal cavity wall 1608 to further minimize the friction between the plunger 1600 and the seal cavity wall 1608.

Figure 17:
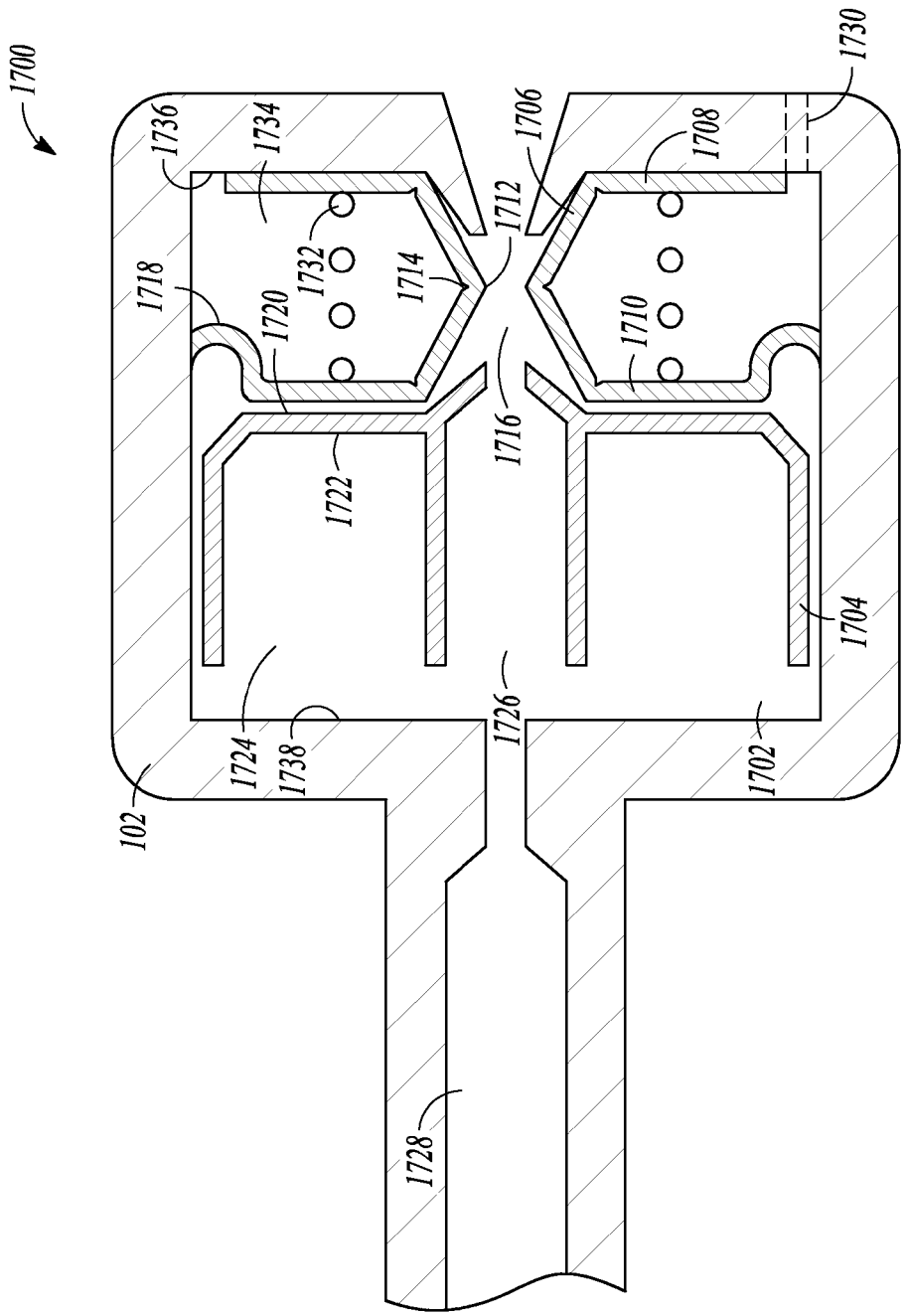
FIG. 17 is a cross-sectional view of one example of a pressure actuated seal assembly having a hinged seal element coupled with a plunger

Referring now to FIG. 17, another example of a pressure actuated seal assembly 1700 is shown, including a plunger 1704 and a seal element 1706. The pressure actuated seal assembly 1700 is positioned within a seal cavity 1702 with the plunger 1704 positioned adjacent to a distal seal cavity surface 1738 and the seal elements 1706 positioned adjacent to a proximal seal cavity surface 1736. The seal element 1706 includes a proximal seal portion 1708 coupled along the proximal seal cavity surface 1736. A distal seal portion 1710 is positioned within the seal cavity 1702 and extends from near the seal element lumen 1716 toward the perimeter of the seal cavity 1702.

In one example shown in FIG. 17, the seal element 1706 includes a rolling diaphragm 1718 coupled between the distal seal portion 1710 and the perimeter of the manifold 102 defining the seal cavity 1702. The rolling diaphragm 1718 allows the distal seal portion 1710 to move proximally and distally within the seal cavity 1702 during sealing and unsealing of the pressure actuated seal assembly 1700. Where the pressure actuated seal assembly 1700 includes the rolling diaphragm 1718 a seal element chamber 1734 is within the seal element 1706. The seal element chamber 1734 is substantially sealed away from the remainder of the seal cavity 1702. In another example, the manifold 102 includes a vent 1730 extending from the exterior of the manifold into the seal element chamber 1734. The vent 1730 allows passage of gases within the seal element chamber 1734 during compression of the seal element 1706 by the plunger 1704.

A biasing member (e.g., a spring, elastomer and the like), is positioned between the proximal seal portion 1708 and the distal seal portion 1710. The biasing member 1732 biases at least the distal seal portion 1710 away from a proximal seal cavity surface 1736. The biasing member 1732 expands the seal element 1706 in a manner similar to an accordion and positions a pinching portion 1712 of the seal element 1706 outwardly from the seal element lumen 1716 to open the seal element lumen 1716 in the absence of pressurized fluid within the manifold 102. The seal element 1706 further includes, in another example, seal element hinges 1714. The seal element hinges 1714 permit deflection of the seal element 1706 (including the pinching portion 1712) inwardly into the seal element lumen 1716 during actuation by the plunger 1704.

The plunger 1704 shown in FIG. 17 includes a plunger proximal face 1720 positioned adjacent to the proximal seal portion 1708. The plunger 1704 further includes a plunger distal face 1722 directed in an opposing direction to the plunger proximal face 1720. The plunger 1704 includes a plunger recess 1724 extending around the plunger lumen 1726, as described in further detail below. In one example, the plunger recess 1724 is sized and shaped to receive a pressurized fluid and transform force from the pressurized fluid into proximal movement of the plunger 1704 to deflect the seal element 1706 and close the seal element lumen 1716.

In operation, when a pressurized fluid is present within the manifold lumen 1728 the pressurized fluid engages against the plunger 1704. For instance, at least a portion of the pressurized fluid is received within the plunger recess 1724. The plunger 1704 is moved proximally away from the distal seal cavity surface 1738 toward a proximal seal cavity surface 1736. Proximal movement of the plunger 1704 deflects the seal element 1706. Pressure applied to the seal element 1706 through the plunger 1704 overcomes the bias provided by the bias member 1732 to the seal element 1706. The distal seal portion 1710 of the seal element 1706 is deflected proximally toward the proximal seal cavity surface 1736. The seal element 1706 acts as a linkage around the seal element hinges 1714 as the distal seal portion 1710 is moved proximally. The pinching portion 1712 compresses around the seal element lumen 1716 and the opposed surfaces of the pinching portion 1712 engage to seal the seal element lumen 1716 and prevent the passage of pressurized fluids through the seal element lumen 1716 and out of the manifold 102. In a similar manner, where an instrument, such as a guide wire, is present within the seal element lumen 1716 pressure upon the plunger 1704 correspondingly deflects the seal element 1706 and moves the pinching portions 1712 inwardly to engage around the instrument. The pinching portions 1712 engage around the instrument and create a seal preventing the passage of pressurized fluids around the instrument and through the seal element lumen. After the pressure is released on the within the manifold lumen 1728 the bias of the biasing member 1732 is no longer opposed by a pressure within the seal cavity 1702. The biasing member 1732 presses the distal seal portion 1710 distally toward the distal seal cavity surface 1738. The plunger 1704 is correspondingly moved toward the distal seal cavity surface 1738 with distal movement of the distal seal portion 1710. The pinching portion 1712 of the seal element 1706 moves outwardly as the biasing member distally moves the distal seal portion 1710 thereby opening the seal element lumen 1716 and allowing passage of the fluids and instruments.

Figure 18A:
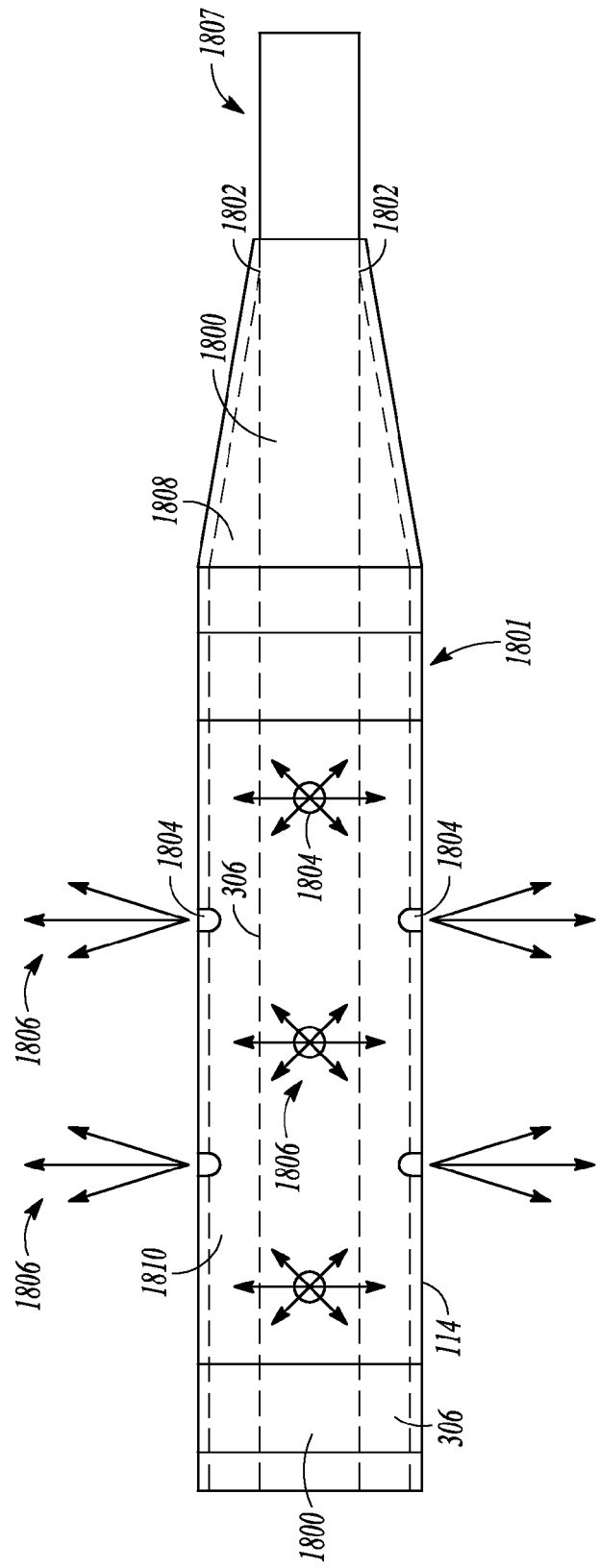
FIG. 18A is a side view of one example of a catheter distal portion including a fluid jet manifold.

Referring now to FIG. 18A, one example of a fluid jet distributor 1801 is shown. As previously described in the examples shown in FIGS. 1 through 17 the pressure actuated seal assemblies are provided within the manifold 102 (FIG. 1). The pressure actuated seal assemblies include seal elements that close a seal element lumen according to the presence of a pressurized fluid within the manifold lumen and the catheter lumen of the catheter. By closing the seal element lumen the pressure actuated seal assemblies maintain a pressurized environment within the catheter 100. A distal portion 114 of the catheter 100 is shown in FIG. 18. The catheter distal portion 114 includes a catheter lumen tapered portion 1808 tapering toward a guide wire orifice 1802 from an interior surface of the catheter defining a catheter lumen intermediate portion 1810. The catheter lumen intermediate portion 1810 extends proximally toward the manifold 102 shown in FIG. 1. Optionally, the catheter lumen tapered portion 1808 gradually tapers over a length of the catheter 100, for instance from near the catheter proximal portion toward the catheter distal portion 114.

A guide wire 1800 is shown positioned within the catheter lumen 306 and extending through the guide wire orifice 1802. Positioning of a portion of the guide wire, for instance the guide wire tip 1807, within the guide wire orifice 1802 partially closes the interior of the catheter and assists in maintaining the pressurized environment within the catheter lumen 306 created in part through operation of the pressure actuated seal assembly within the manifold 102. The guide wire orifice 1802 includes a perimeter substantially matching the perimeter of the guide wire tip 1807 with sufficient tolerance to allow movement of the guide wire tip through the orifice. Positioning the guide wire tip 1807 within the guide wire orifice 1802 closely fits the catheter distal portion 114 around the guide wire tip 1807 and minimizes fluid flow through the guide wire orifice 1802 from the catheter lumen tapered portion 1808 to the environment surrounding the catheter 100.

In one example, the catheter distal portion 114 includes pressurized fluid passages 1804 provided in at least one of the catheter lumen tapered portion 1808 and the portion of the catheter body including the catheter lumen intermediate portion 1810. Referring to FIG. 18, the pressurized fluid passages 1804 are shown in broken lines in the catheter lumen intermediate portion 1810. The guide wire 1800 is positioned within the guide wire orifice 1802 and acts as a plug to substantially prevent the passage of pressurized fluid through the guide wire orifice. The pressure actuated seal assemblies described herein ensure pressurized fluid does not pass through the seal element lumen. The pressurized fluid is instead forced through the pressurized fluid passages 1804 and directed into fluid jets 1806. The fluid jets 1806 are used, in one example, to engage with and break up thrombus material within a vessel. In another example, the fluid jets 1806 marinate the surrounding vasculature with medication, contrast fluid and the like fed to the catheter distal portion. In one option, high pressure delivery of fluids, for instance during thrombectomy procedures, is halted while the medication or contrast fluid is delivered through the catheter lumen 306 and the fluid passages 1804. The pressurized fluid is delivered through the fluid passages over a range of pressures including, but not limited to, pressures sufficient to deliver the fluids through the passages 1804 to the vessel location, and higher pressures for delivery of the fluid and removal of thrombus.

The pressurized environment within the catheter lumen 306 provides a substantially similar pressure at the catheter distal portion 114 compared to the catheter proximal portion 112 in close proximity to the pressure actuated seal assemblies. The catheter body 104 maintains this pressurized environment throughout the catheter body 104 without substantial pressure losses from the catheter proximal portion 112 to the catheter distal portion 114 because the catheter body 104 is spaced away from the interior of the catheter lumen 306. For instance, as shown in FIG. 18 the guide wire 1800 near the center of the catheter body 104 is spaced from the walls of the catheter body 104. The large diameter of the catheter body 104 from the catheter proximal portion 112 to the catheter distal portion 114 minimizes pressure losses due to turbulent flow and other fluid behavior along the surfaces circumscribing the catheter lumen 306. The catheter lumen 306 is large enough to isolate pressure losses along the circumscribing surfaces of the catheter lumen 306 and maintain a consistent pressure within the interior of the catheter lumen 306 from the catheter body proximal portion 112 to the catheter body distal portion 114. The pressure actuated seal assemblies described previously thereby cooperate with the catheter body 104 and the catheter lumen 306 to provide a pressurized environment throughout the catheter body including the catheter body distal portion 114. The cooperation of the pressure actuated seal assemblies with the catheter lumen 306 thereby maintains a high pressure at the catheter body distal portion to produce the fluid jets 1806 through the pressurized fluid passages 1804.

Figure 18B:
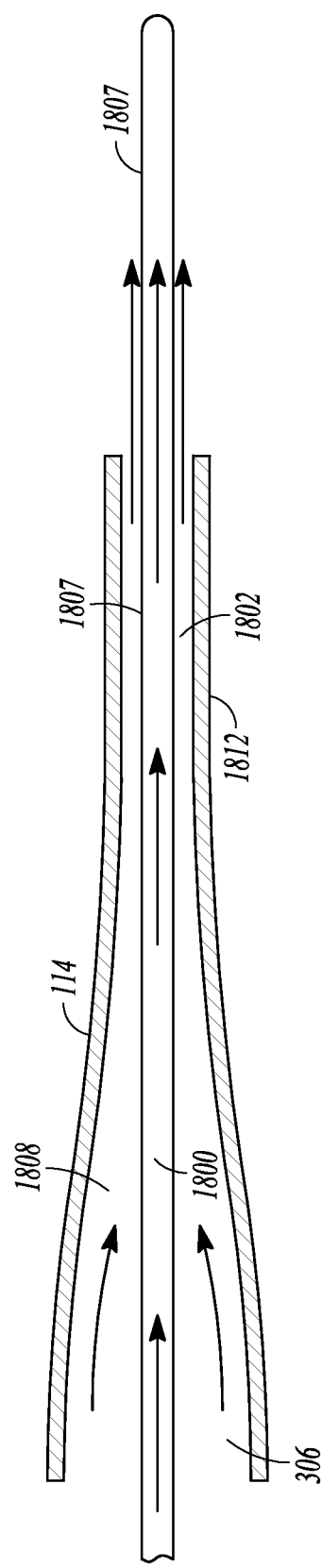
FIG. 18B is a cross-sectional view of another example of a catheter distal portion including a distal fluid jet system.

Another example of a fluid jet system 1812 is shown in FIG. 18B. The fluid jet system 1812 does not include the fluid passages 1804 shown in FIG. 18A for the fluid jet distributor 1801. Instead, the fluid jet system 1812 uses the guide wire orifice 1802 as a nozzle to deliver a fluid jet distally from the catheter distal portion 114. As described above with regard to the fluid jet distributor 1801, in one example, the guide wire orifice 1802 has a tight tolerance relative to the guide wire tip 1807, and reception of the guide wire tip 1807 within the guide wire orifice 1802 plugs the orifice and prevents the distribution of fluids. In another example, the guide wire orifice 1802 is larger than the outer diameter of the guide wire tip 1807 and fluid is deliverable between the guide wire tip 1807 and the surfaces defining the guide wire orifice. Axial movement of the guide wire 1800 within the catheter body distal portion 114 including movement of the guide wire tip 1807 through the guide wire orifice 1802 controls the flow rate and pressure of delivery according to the relative opening between the guide wire tip and the surfaces defining the guide wire orifice 1802. Stated another way, movement of the guide wire tip 1807 gradually into and out of the guide wire orifice 1802 correspondingly alters the spacing between the guide wire tip 1807 and the surfaces of the orifice (due in part to the taper of the catheter lumen tapered portion 1808 and the varying distance between the guide wire tip and the tapered portion).

In operation, the fluid jet system 1812 is positioned on the catheter body distal portion 114 and positioned at a desired location within the vasculature. For example, the catheter body 104 (see FIG. 1) is guided along the guide wire 1800. The specialist may then deliver fluids including, but not limited to, medications, contrast media and the like to the catheter body distal portion 114 under pressure. Procedures, including thrombectomy procedures, making use of the catheter lumen 306 are arrested, while the fluid is delivered. Because the fluid is delivered under pressure the pressure actuated seal assemblies (described herein) seal the catheter lumen 306 at the proximal portion of the catheter and maintain a pressurized environment within the lumen for delivery of the fluid to the catheter distal portion 114.

Where the guide wire orifice 1802 has a tight tolerance with the guide wire tip 1807 the specialist withdraws the guide wire tip from the orifice and the fluid is delivered through the guide wire orifice. In the option having space between the guide wire tip 1807 and the surfaces of the guide wire orifice 1802 (e.g., where the catheter includes one or more of the catheter lumen tapered portion 1808 and a gap between the guide wire tip and the orifice) pressurized fluid is delivered through the space. The specialist may adjust the delivery pressure and flow rate as needed according to axial positioning of the guide wire tip 1807 relative to the guide wire orifice 1802. For instance, fluids are delivered with higher pressure and greater velocity (with a correspondingly strong jet) where a small space is formed between the guide wire tip 1807 and the guide wire orifice 1802 surface. Greater flow rate is achieved where the guide wire tip 1807 is withdrawn, at least partially or more, from the guide wire orifice 1802 surfaces thereby increasing the gap between the catheter and the guide wire tip. As described above with regard to the fluid jet distributor 1801, the fluid jet system 1812 delivers fluids over a range of pressures including, but not limited to, pressures sufficient to deliver the fluids through the guide wire orifice 1802 to the vessel location, and higher pressures for delivery of the fluid and removal of thrombus.

Figure 18C:
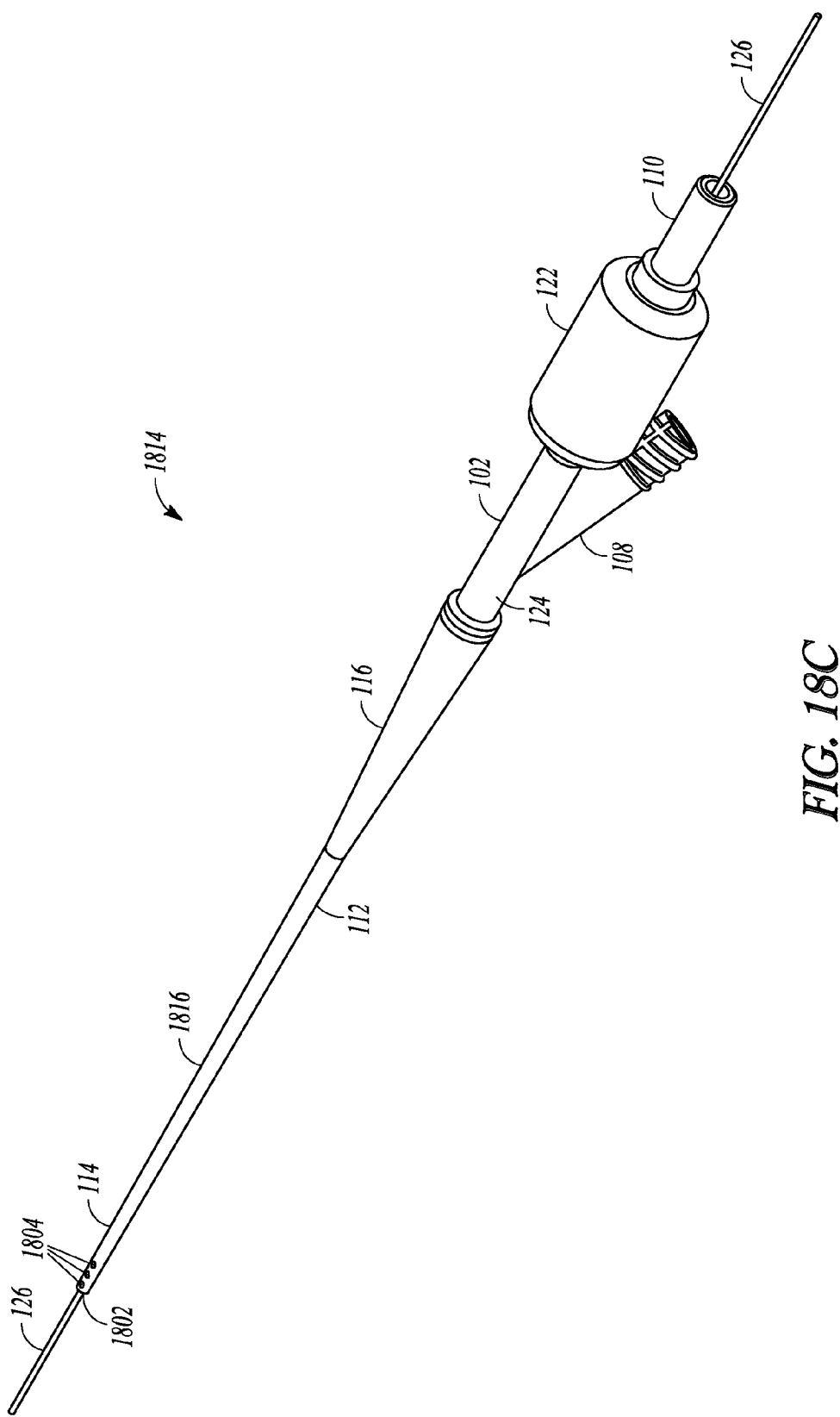
FIG. 18C is a side perspective view of one example a catheter including a tapering catheter shaft.

Another example of a catheter 1814 is shown in FIG. 18C. The catheter 1814 includes the previously described fluid passages 1804 for distribution of fluid from the catheter distal portion 114. The catheter body 1816 is tapered from near the manifold 102 toward the catheter distal portion 114. The tapered catheter body 1816 includes a corresponding tapered catheter lumen that gradually tapers toward the catheter distal portion 114. The taper of the catheter body 1816 ensures that there is a gap between the inner wall of the catheter lumen and the guide wire 126 to permit fluid flow along the catheter to the fluid passages 1804 and the guide wire orifice 1802. Stated another way, by providing a tapered gap in the catheter body 1816 pressure losses due to throttling of flow around the guide wire 126 are minimized. Fluids (medication, contrast and the like) are thereby readily delivered to the catheter distal portion 114 and the surrounding vasculature even while an instrument (e.g., guide wire 126) is present within the catheter body 1816. Further, the catheter 1814 with the tapered catheter body 1816 has enhanced deliverability because the distal portion of the catheter (near the catheter distal portion 114 and extending toward the catheter proximal portion 112) has a small cross sectional area and is correspondingly more flexible and able to easily navigate vasculature relative to the larger proximal portion of the catheter body 1816.

Figure 19:
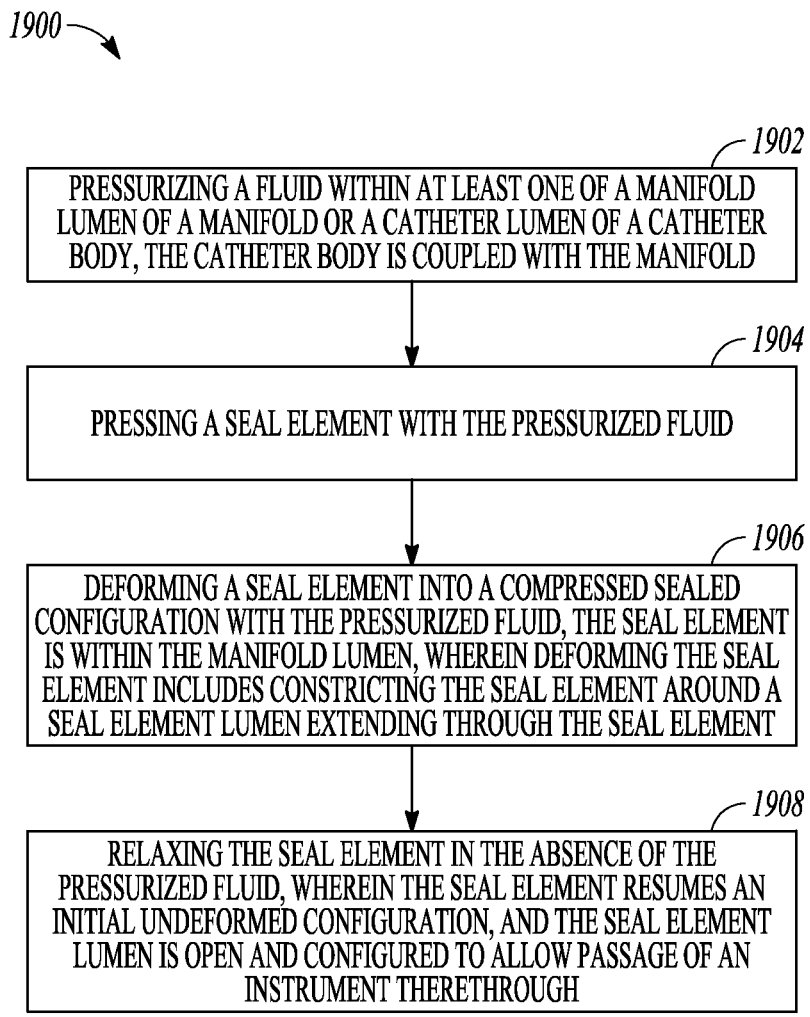
FIG. 19 is a block diagram showing one example of a method for using a pressure actuated seal assembly.

Referring now to FIG. 19, one example of a method 1900 for using a catheter including a pressure actuated seal assembly is shown. Reference is made in the description of the method 1900 to various elements previously shown in FIGS. 1-18. Where reference is made to one element, the reference is intended to be exemplary and implicitly includes other similar elements herein and their equivalents. At 1902, a fluid is pressurized within at least one of a manifold lumen 304 or a manifold 102 or catheter lumen 306 of a catheter body 104. The catheter body 104 is coupled with the manifold 102. At 1904, a seal element, such as a seal element within a pressure actuated seal assembly (e.g., pressure actuated seal assembly 202 shown in FIG. 2), is pressed by the pressurized fluid within one or more of the catheter lumen 306 and manifold lumen 304. At 1906 the pressurized fluid deforms the seal element into a compressed sealed configuration. Deforming the seal element 206 includes constricting the seal element around the seal element lumen 302 extending through the seal element 206. As previously described above, the pressure exerted by the pressurized fluid on the seal element compresses the seal element in a proximal direction toward a manifold proximal portion 122. Proximal seal element compression causes inward compression of the seal element 206 into the seal element lumen 302. The inward compression closes the seal element lumen. In still another example, deforming the seal element includes constricting the seal element 206 around an instrument positioned within the seal element lumen 302 (e.g. a guide wire, an introducer and the like) to provide a seal between the seal element and the instrument. At 1908, the seal element 206 is relaxed in the absence of the pressurized fluid. The seal element 206 resumes an initial undeformed configuration and the seal element lumen is correspondingly opened and configured to allow passage of an instrument. Stated another way, the seal element 206 is biased from the compressed configuration into an original undeformed configuration (e.g., by the natural elasticity of the seal element, a biasing member and the like). In the original configuration the seal element 206 withdraws from the seal element lumen and opens the seal element lumen for passage of instruments.

Several options for the method 1900 follow. In one example, pressing the seal element 206 includes pressing an amplifier, such as the amplifier 208, against the seal element 206. The amplifier 208 multiplies the force of the pressurized fluid transmitted to the seal element 206. For instance, the amplifier includes a first amplifier face 214 substantially larger than the second amplifier face 216. The first amplifier face 214 is directed toward the pressurized fluid and the second amplifier face 216 is directed toward the seal element 206. Force applied to the first amplifier face 214 by the pressurized fluid is transmitted through the amplifier 208 to the second amplifier face adjacent to the seal element 206 and smaller than the first amplifier face. The force transmitted through the amplifier 208 from the large first amplifier face is multiplied at the smaller second amplifier face 216 and is transmitted into the seal element 206. In another example, deforming and constricting the seal element, such as the seal element 1304 having at least one deformable lip 1306, includes constricting the deformable lip 1306 around the seal element lumen 1312.

In still another example, the method 1900 includes distributing a fluid including, but not limited to, medication, contrast, saline and the like through the catheter distal portion 114, for instance through pressurized fluid passages 1804 (see 18A). Optionally, a fluid is distributed through a guide wire orifice 1802 as shown in FIG. 18B. The pressure actuated seal assemblies close a seal lumen and optionally close the seal around an instrument disposed in the seal lumen including a guide wire (e.g., guide wire 126, shown in FIG. 1). The sealed environment prevents the flow of the fluids through the manifold 102 and instead directs flow of the fluids along the catheter body 104 toward a fluid jet distributor 1801 including the pressurized fluid passages 1804 and the guide wire orifice 1802. In another example, the fluid is distributed under high pressure to impinge upon thrombus material and break up the material. In yet another example, the fluid is distributed at a lower pressure to marinate the vessel region surrounding the fluid jet distributor 1801. The instrument, such as the guide wire, at least partially closes the guide wire orifice 1802 to direct the flow of fluid into at least one of the pressurized fluid passages 1804 and through the guide wire orifice 1802 partially closed with the guide wire.

Figure 20:
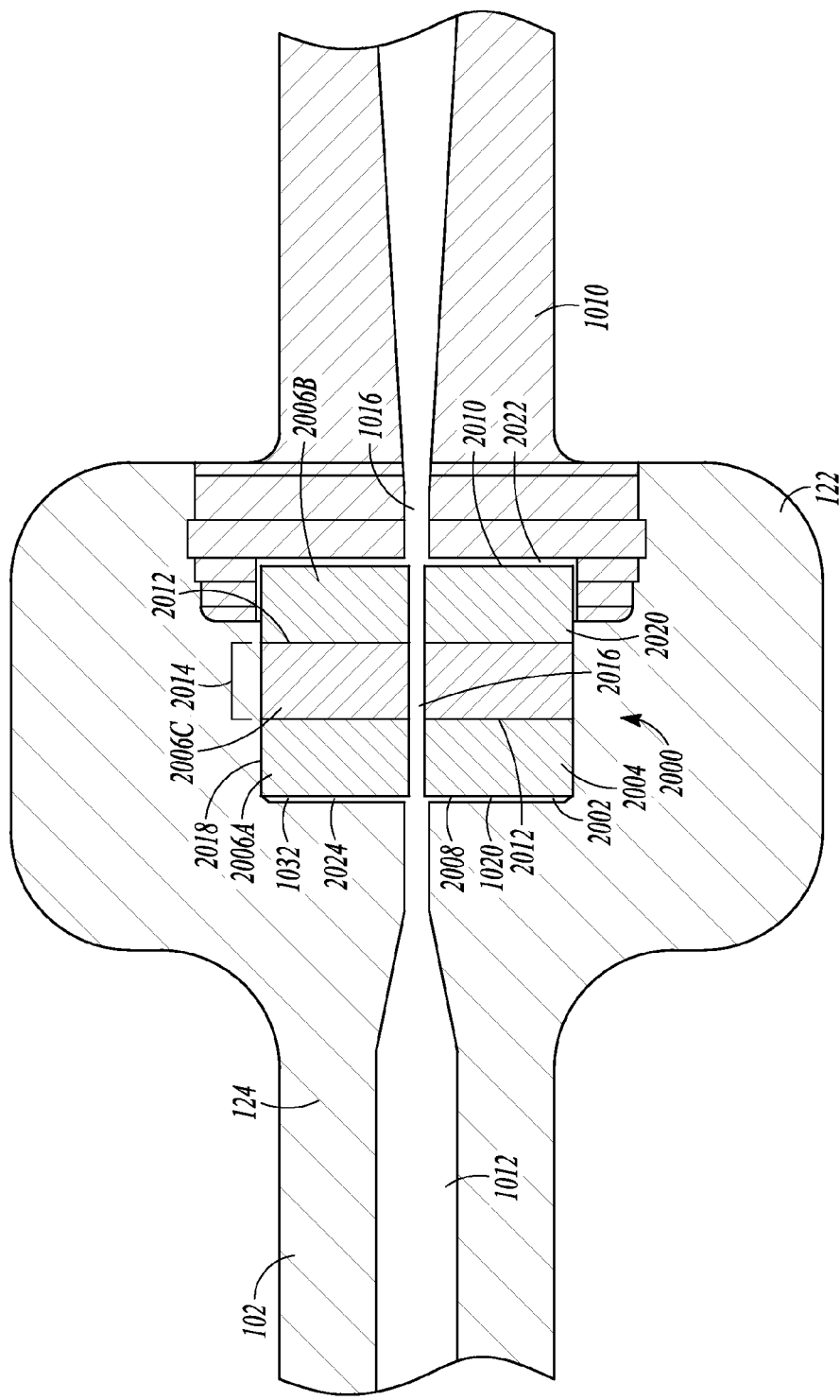
FIG. 20 is a cross-sectional view of one example of a pressure actuated seal assembly having a plurality of seal portions.

FIG. 20 shows another example of a pressure actuated seal assembly 2000. As previously described in other examples, the pressure actuated seal assembly 2000 is included within the manifold, such as the manifold 102. The manifold 102 is substantially similar to previously described manifolds. For instance, the manifold 102 includes a manifold proximal portion 122 and a manifold distal portion 124. As shown in FIG. 20, the manifold 102 includes a seal cavity 2002 sized and shaped to receive a seal element 2004 therein. An introducer guide 1010, in one example, is positioned within the manifold distal portion 124 and closes the seal cavity 2002 to retain the seal element 2004 therein. Further, in the example show the introducer guide 1010 provides the proximal end of the seal cavity 2022.

Referring again to FIG. 20, the seal element 2004 includes first, second and third seal portion 2006A, B, C, respectively.

The first, second and third seal portions 2006A-C are orientated in a series within the seal cavity 2002. As shown, each of the seal portions includes a portion of the seal element lumen 2016 extending therethrough. As previously described, the seal element lumen 2016 is aligned with the manifold lumen 1012 and the introducer lumen 1016 to form a substantially continuous lumen through the manifold 102 and the seal element 2004. The seal element perimeter 2018 cooperates with the seal cavity perimeter 2020 to substantially align the first, second and third seal portions 2006A, B, C within the seal cavity 2002 and thereby align the seal element lumen (e.g., lumens of each of the portions) with the manifold lumen 1012 and the introducer lumen 1016.

As described above, the seal element 2004 includes a plurality of portions including, for instance first, second and third seal portions 2006A, B, C. In one example, the first, second and third seal portions 2006A-C are constructed with varying materials with correspondingly different durometers. For instance, each of the first, second and third seal portions are constructed with pliable materials configured to deflect as pressure is applied across, for instance, a first seal face 2008 of the first seal portion 2006A through the slit 1032 between the distal end of the seal cavity 2024 and the first seal face 2008. For instance, as pressure is applied across the first seal face 2008 the first seal portion 2006A is pressed toward the second and third seal portions 2006B, C and compresses each of the seal portions through engagement of intermediate seal faces 2012 and thereby inwardly compresses the first, second and third seal portions 2006A-C around the seal element lumen 2016. Optionally, compression of the first, second and third seal portions 2006A-C similarly expands the seal portions outwardly and engages the seal element perimeter 2018 with the seal cavity perimeter 2020 to substantially prevent the flow of pressurized fluid around gaps otherwise formed between the first through third seal portions 2006A-C and the seal element perimeter 2018.

As described above the first, second and third seal portions 2006A-C are each constructed with different materials having different durometers. In one example, the first seal portion 2006A is constructed with a first material having a first durometer while the second and third seal portions 2006B, C include materials having second and third respective materials each with different durometers. Optionally, the first and second seal portions 2006A, B include materials having a durometer greater than the durometer of the intermediate third seal portion 2006C. The first and second seal portions 2006A, B thereby form a seal chamber 2014 that substantially contains the third seal portion 2006C therebetween. In one example, the seal chamber 2014 including the first and second seal portions 2006A, B maintains the third seal portion 2006C in the configuration shown in FIG. 20 and substantially prevents the flow (extrusion) of the third seal portion 2006C through either of the manifold lumen 1012 and the introducer of the lumen 1016 (or the portions of the seal element lumen 2016 associated with the first and second seal portions). For instance, where the third seal portion 2006C is constructed with a material similar to a gel the seal chamber 2014 including more rigid seal portions 2006A, B provides structural support to the seal portion 2006C and substantially prevents the flow of the third seal portion through the seal element lumen 2016.

In another example, the first seal portion 2006A is constructed with a material with a greater durometer than that of the third seal portion 2006C and the first seal portion 2006A acts as an amplifier when engaged with pressurized fluid, for instance, along the first seal face 2008. The first seal portion 2006A is pressed into engagement with the third seal portion 2006C and compresses the more pliable third seal portion 2006C to collapse the seal portion 2006C around the seal element lumen 2016. Optionally, each of the first, second and third seal portion 2006A-C compresses inwardly (and outwardly in some examples) under differing pressures. For instance, at lower pressures such as less than 50 psi the intermediate third seal portion 2006C having a lower durometer initially expands inwardly to close the seal element lumen 2016 for instance around an instrument positioned within the seal element lumen. At a higher pressure, for instance, 50 to 1200 psi the third seal portion 2006C as well as one of the first and second seal portions 2006A, B (based on the durometers of each of the seal portions) compresses with the third seal portion 2006C to compress the seal materials around the seal element lumen 2016 including, for instance, an instrument disposed therein. At even higher pressures, such as at 1200 to 1500 psi each of the first, second and third seal portions 2006A-C is compressed by the pressurized fluid applied along the first seal face 2008, for instance, through transmission of compression through intermediate seal faces 2012 engaged between the seal portions. Each of the seals compresses inwardly around the seal element lumen 2016 to close the seal element lumen 2016 or engage the seal portions around an instrument provided within the seal element lumen 2016. Optionally, the seal portions 2006A-C are configured to only provide a seal when an instrument is disposed within the seal element lumen 2016 and otherwise allow throttled flow of fluid (e.g., for purging of a catheter system) through the lumen.

In other examples, the materials of the first, second and third seal portions 2006A-C are selected with a variety of durometers to tune the response of the seal element 2004 to seal with one or more of the seal portions 2006A-C under varying pressures. One such example is provided immediately above. In one prophetic example, the first seal portion 2006A includes a first material having a durometer of approximately 60, the second seal portion includes a durometer of approximately 30 and the third seal portion 2006C includes a more pliable durometer of approximately 10.

The pressure actuated seal assemblies and methods for using the same described herein automatically seal a seal element lumen in the presence of a pressurized fluid without requiring hand operation from a catheter operator. The operator does not need to operate the seal or observe an indicator to know the pressure actuated seal assembly is sealed and closing the seal element lumen. Instead, when a pressurized fluid is introduced to the catheter and manifold for use as part of a procedure the seal assembly automatically closes because of the pressure. The operator can thereby confidently operate the catheter without doubting whether the seal has closed the seal element lumen or the seal was not actuated because of operator error. Additionally, because the seal element is actuated according to the fluid pressure within the catheter the seal becomes correspondingly tighter with increasing fluid pressures. A seal is thereby maintained within the seal element lumen across a range of pressures. For instance, the pressure actuated seal assemblies described herein provide a complete seal from at least 10 to 1200 psi. Optionally a complete seal is maintained over pressures greater than 1200 psi. Similarly, the pressure actuated seal elements automatically unseal in the absence of a pressurized fluid freeing the operator from manipulating seal element into an open configuration.

Further, the seal element is capable of closing the seal element lumen with or without an instrument therein. The seal element seals around a variety of instrument sizes and configurations (guidewires with varying diameters, multiple instruments and the like). For instance, a single seal element will seal around a variety of instruments with different perimeters when under pressure from fluid in the catheter body. In another example, the seal element material and seal element lumen size are chosen according to the size of the instrument delivered through the seal element. Stated another way, the seal element is chosen to ensure tight sealing around a specified instrument when the seal element is subjected to pressure from the pressurized fluid in the catheter body.

If a procedure requires the presence of an instrument within the catheter while the pressurized environment is maintained the instrument is fed into the catheter through the seal element. As the pressurized fluid applies pressure to the seal element the seal element closes and seals around the instrument. Optionally, sealing of the seal element fixes the instrument in place and correspondingly retains the instrument in a desired orientation according to the needs of the operator. In another example, the instrument is slidable through the closed seal element if movement of the instrument is necessary while the fluid is pressurized in the catheter. In any case, when the fluid in the catheter body is no longer pressurized and the seal element is open and the instrument is easily slidable through the seal element lumen.

Moreover, the seal elements and the surrounding manifolds are configured to permit back loading and front loading of instruments (e.g., feeding the instrument into the catheter from the manifold and feeding the instrument toward the manifold from the catheter, respectively). For instance, one or more of the manifold and the seal element include tapering surfaces that guide the instrument through the seal element lumen when front or back loaded.

In one example, the instrument includes an introducer having its own lumen and a second instrument is fed through the introducer into the pressurized environment of the catheter. Sealing the seal element around the introducer thereby provides access through the catheter to vasculature while pressure is maintained within the catheter. Optionally, the instrument within the introducer is snuggly engaged by the interior surface of the introducer and slidable relative to the introducer. The instrument and introducer are sized and shaped to minimize the space therebetween to substantially prevent the passage of pressurized fluids through the introducer while still allowing movement of the instrument through the seal.

As previously described, the pressure actuated seal assemblies maintain a pressurized environment within the catheter lumen during operation of the catheter, for instance, during a thrombectomy procedure where high pressure fluids are fed through the catheter body. Pressurized fluid is transmitted through the catheter lumen to the catheter distal portion. The catheter lumen tapers into a fluid jet manifold and the pressurized fluid is directed through pressurized fluid passages into fluid jets that project from the catheter body. Because the catheter interior wall only tapers near the catheter distal portion pressure losses are minimized between the catheter proximal and distal portions. The catheter lumen tapers near the catheter distal portion to enhance the strength of the fluid jets projecting from the pressurized fluid passages. Similarly, where an instrument is present within the catheter lumen (e.g., a guide wire) the catheter interior wall is spaced from the instrument to minimize pressure losses between the wall and the instrument. Stated another way, flow characteristics including turbulent flow extending between the catheter interior wall and the instrument are avoided. The pressure within the catheter lumen is thereby substantially maintained from the catheter proximal portion to the catheter distal portion.

Although the present disclosure has been described in reference to preferred embodiments and methods for use of those embodiments, persons skilled in the art will recognize that changes may be made in form and detail without departing from the spirit and scope of the present disclosure. It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present application. Further, the elements and features of one or more of the pressure actuated seal elements and the associated structures and functions of the seal elements is fully compatible with other fluid delivery devices including, but not limited to, handheld manifolds, access ports and independent catheters. Stated another way, the pressure actuated seal elements are not limited to direct or integral coupling or incorporation to a catheter. The scope of the present disclosure should, therefore, be determined with reference to the appended claims, along with the full scope of equivalents to which such claims are entitled.

What is claimed is:

1. A pressure actuated seal assembly comprising:
   a manifold, the manifold including a seal cavity, and a manifold lumen extends through the manifold and the seal cavity;
   a pressure actuated seal element positioned within the seal cavity, the seal element includes:
      a first seal face in communication with the manifold lumen,
      a second seal face opposed to the first seal face, and
      a seal element lumen extending from the first seal face to the second seal face, the seal element lumen is in communication with the manifold lumen;
   an amplifier coupled with the seal element, the amplifier includes first and second amplifier faces with respective first and second surface areas, the first surface area larger than the second surface area, and the second amplifier face is coupled with the first seal face; and
   the pressure actuated seal element is deformable between an open configuration and a sealed configuration, wherein:
      in the sealed configuration, a pressurized fluid in at least the manifold lumen presses on the first amplifier face and generates a first force and the second amplifier face presses on the first seal face with a second force greater than the first force according to the larger first surface area relative to the second surface area, and the pressure actuated seal element compresses inwardly around the seal element lumen according to the greater second force, and
      in the open configuration, the pressure actuated seal element relaxes in an absence of the pressurized fluid, and the seal element lumen is open and configured to allow passage of an instrument therethrough.

2. The pressure actuated seal assembly of claim 1, wherein the pressure actuated seal element includes a deformable lip surrounding the seal element lumen, and the deformable lip includes at least portions of the first and second seal faces.

3. The pressure actuated seal assembly of claim 1, wherein at least the first seal face tapers from an intermediate seal portion toward a distal seal portion, and the first seal face has a greater area than a cross-section of the seal cavity.

4. The pressure actuated seal assembly of claim 1, wherein the second seal face tapers from an intermediate seal portion toward a proximal seal portion, and the seal cavity tapers from near the intermediate seal portion toward the proximal seal portion, and the tapered seal cavity is sized and shaped to receive the pressure actuated seal element.

5. The pressure actuated seal assembly of claim 1, where the instrument is positioned within the seal element lumen of the pressure actuated seal element, in the sealed configuration, the pressure actuated seal element seals around the instrument.

6. The pressure actuated seal assembly of claim 1, wherein pressing on the first seal face toward the second seal face compresses the pressure actuated seal element outwardly into sealing engagement with a seal cavity perimeter.

7. The pressure actuated seal assembly of claim 1, wherein the pressure actuated seal element includes a first seal portion including the first seal face, a second seal portion including the second seal face and a third seal portion intermediate to the first and second seal portions, and one or more of the first, second and third seal portions has a hardness different from another of the seal portions.

8. The pressure actuated seal assembly of claim 1, wherein in the open configuration the amplifier is biased away from the second seal face with a biasing element interposed between the amplifier and the seal element.

9. The pressure actuated seal assembly of claim 8, wherein the biasing element is a spring.

10. The pressure actuated seal assembly of claim 1, wherein the amplifier is slidable within the seal cavity.

11. The pressure actuated seal assembly of claim 1, wherein the second amplifier face and the seal element are received within a recess within the seal cavity.

12. A catheter assembly comprising:
a self-sealing manifold, the manifold includes a seal cavity, and a manifold lumen extends through the manifold and the seal cavity;
a tapered catheter body coupled with the self-sealing manifold, the tapered catheter body includes a taper over at least a portion of a catheter body length including a catheter distal portion, the tapered catheter body includes a catheter lumen in communication with the manifold lumen, wherein the manifold lumen and the catheter lumen are configured to receive pressurized fluids; and
the self-sealing manifold includes a seal assembly positioned within the seal cavity, and the seal assembly seals the manifold lumen and the catheter lumen near the self-sealing manifold in a presence of the pressurized fluids within at least one of the manifold lumen and the catheter lumen, the seal assembly includes:
a seal element within the seal cavity, the seal element includes first and second seal faces,
an amplifier within the seal cavity distal to the seal element, the amplifier includes first and second amplifier faces with respective first and second surface areas, the first surface area larger than the second surface area, and the second amplifier face is coupled along the first seal face, and
wherein a first force is applied to the first amplifier face by the pressurized fluids, and a corresponding second force is applied from the second amplifier face to the seal element at the first seal face, the second force greater than the first force according to the larger first surface area relative to the second surface area.

13. The catheter assembly of claim 12, wherein the catheter distal portion includes one or more fluid passages, and a fluid is distributed from the one or more fluid passages when the pressurized fluids are received within the manifold and catheter lumens and the seal assembly seals the manifold lumen and the catheter lumen near the self-sealing manifold.

14. The catheter assembly of claim 13, wherein the one or more fluid passages include a plurality of fluid passages extending through a catheter sidewall.

15. The catheter assembly of claim 14 further comprising an instrument slidably positioned within a guide wire orifice and operable to plug the guide wire orifice and divert the fluid through the plurality of fluid passages.

16. The catheter assembly of claim 12, wherein a biasing element is interposed between the amplifier and the seal element, and the biasing element biases the amplifier away from the seal element.

17. The catheter assembly of claim 12, wherein the amplifier is slidable within the seal cavity.

18. The catheter assembly of claim 12, wherein the second amplifier face and the seal element are received within a recess within the seal cavity.

19. A catheter assembly comprising:
a manifold, the manifold includes a manifold lumen having a manifold lumen perimeter, the manifold lumen extends through the manifold;
wherein the manifold includes an elongate seal cavity in communication with the manifold lumen, the elongate seal cavity extends longitudinally from a seal cavity proximal end to a seal cavity distal end, a seal cavity perimeter circumscribes the elongate seal cavity, and the seal cavity perimeter is larger than the manifold lumen perimeter;
a pressure actuated seal element within the elongate seal cavity, the seal element includes:
a first seal face,
a second seal face opposed to the first seal face, and
a seal element lumen extending from the first seal face to the second seal face, the seal element lumen is in communication with the manifold lumen;
an amplifier interposed between the first seal face and the seal cavity distal end, the amplifier includes first and second amplifier faces with respective first and second surface areas, the first surface area larger than the second surface area, and the second amplifier face is engaged with the first seal face; and
wherein a first force is applied to the first amplifier face by a pressurized fluid between the first amplifier face and the seal cavity distal end, and a corresponding second force is applied from the second amplifier face to the seal element at the first seal face, the second force greater than the first force according to the larger first surface area relative to the second surface area, the pressure actuated seal element is configured to deform according to the greater second force, and the pressure actuated seal element compresses inwardly around the seal element lumen according to the greater second force.

20. The catheter assembly of claim 19, wherein at least the first seal face tapers from an intermediate seal portion toward a distal seal portion, and the first seal face has a greater surface area than a cross-section of the seal cavity.

21. The catheter assembly of claim 19, wherein the second seal face tapers from an intermediate seal portion toward a proximal seal portion, and the seal cavity tapers from near the intermediate seal portion toward the proximal seal portion, and the tapered seal cavity is sized and shaped to receive the pressure actuated seal element.

22. The catheter assembly of claim 19, wherein the pressure actuated seal element is configured to deform when an instrument is positioned within the seal element lumen and the pressurized fluid is between the first amplifier face and the seal cavity distal end, the seal element compresses inwardly and seals around the instrument.

23. The catheter assembly of claim 19, wherein compressing the first seal face toward the second seal face compresses the pressure actuated seal element outwardly into sealing engagement with the seal cavity perimeter.

24. The catheter assembly of claim 1, wherein the pressure actuated seal element includes a first seal portion including the first seal face, a second seal portion including the second seal face and a third seal portion intermediate to the first and second seal portions, and one or more of the first, second and third seal portions has a hardness different from another of the seal portions.

25. The catheter assembly of claim 24, wherein the first seal portion includes a first portion hardness greater than a second portion hardness of the second seal portion, and the first portion hardness is greater than a third portion hardness of the third seal portion.

26. The catheter assembly of claim 25, wherein the second portion hardness is greater than the third portion hardness.

27. The catheter assembly of claim 24, wherein the pressure actuated seal element includes a seal chamber comprising the first and second seal portions, and the seal chamber contains the third seal portion.

28. The catheter assembly of claim 27, wherein the seal chamber constrains the third seal portion from flowing past the first and second seal portions.

29. The catheter assembly of claim 19, wherein a biasing element is interposed between the amplifier and the seal element, and the biasing element biases the amplifier away from the seal element.

30. The catheter assembly of claim 19, wherein the second amplifier face and the seal element are received within a recess within the seal cavity.

\* \* \* \* \*